(12) United States Patent
Kozak et al.

(10) Patent No.: US 7,186,703 B2
(45) Date of Patent: Mar. 6, 2007

(54) DERIVATIVES OF BRANCHED-CHAIN LIPOPHILIC MOLECULES AND USES THEREOF

(75) Inventors: Alexander Kozak, Rehovot (IL); Marina Vinnikova, Ramla (IL); Michael Polyak, Bnei-Ayish (IL); Eliezer Beit-Yannai, Jerusalem (IL); Dalia Reznitsky-Cohen, Nes-Ziona (IL); Alexander Senderikhin, Ashdod (IL)

(73) Assignee: D-Pharm Ltd., Rehovot (IL)

( * ) Notice: Subject to any disclaimer, the term of this patent is extended or adjusted under 35 U.S.C. 154(b) by 295 days.

(21) Appl. No.: 10/343,105

(22) PCT Filed: Aug. 1, 2001

(86) PCT No.: PCT/IL01/00713

§ 371 (c)(1),
(2), (4) Date: Jan. 27, 2003

(87) PCT Pub. No.: WO02/11666

PCT Pub. Date: Feb. 14, 2002

(65) Prior Publication Data

US 2003/0186897 A1 Oct. 2, 2003

(30) Foreign Application Priority Data

Aug. 3, 2000 (IL) ..................... 137672

(51) Int. Cl.
*A61K 31/661* (2006.01)
*C07F 9/09* (2006.01)
(52) U.S. Cl. ............ 514/114; 514/120; 558/169; 558/177; 558/178; 558/179
(58) Field of Classification Search ........... 558/167, 558/169, 170, 177, 178, 179; 514/114, 120, 514/129
See application file for complete search history.

(56) References Cited

U.S. PATENT DOCUMENTS

| | | | |
|---|---|---|---|
| 3,260,688 | A | 7/1966 | Makino et al. |
| 4,300,903 | A | 11/1981 | Engelhardt et al. |
| 4,623,743 | A | 11/1986 | Kurosaki et al. |
| 4,670,575 | A | 6/1987 | Kurosaki et al. |
| 4,736,051 | A | 4/1988 | Wakatsuki et al. |
| 4,751,320 | A | 6/1988 | Masuda et al. |
| 5,679,459 | A | 10/1997 | Riess et al. |
| 5,686,540 | A * | 11/1997 | Kakizawa ............ 525/444 |
| 5,846,516 | A | 12/1998 | Riess et al. |
| 6,030,961 | A | 2/2000 | Nudelman et al. |

FOREIGN PATENT DOCUMENTS

| | | |
|---|---|---|
| DE | 2335901 | 2/1974 |
| DE | 3506973 | 9/1985 |
| DE | 3609492 | 9/1986 |
| DE | 3639084 | 6/1987 |
| EP | 0023341 | 2/1981 |
| EP | 0157210 | 10/1985 |
| GB | 1431932 | 4/1976 |
| JP | 56077218 | 6/1981 |
| JP | 60072829 | 4/1985 |
| JP | 61129189 | 6/1986 |
| JP | 62177008 | 8/1987 |
| JP | 09255553 | * 9/1997 |
| WO | WO 92/21688 | 12/1992 |

OTHER PUBLICATIONS

Database CAS ONLINE on STN, Chem. Abstr., accession No. 1966:404220, Juk'yanov et al., Doklady Adademii Nauk SSSR (1965), 165(1), 121-4.*
The JP translation is included.*
Obach R. S., Drug—drug interactions: An important negative attribute in drugs, Drugs of Today, 39(5), 301-38, (2003).*
Database Crossfire Beilstein 'Online!. Beilstein Institut zur Forderung der Chemishchen Wissenschaften, XP002267929, databse accession No. BRN 1817947, Ferraro, et al., J. Inorg. Nucl. Chem., vol. 27, pp. 2055-2058, 1965.
Database Crossfire Beilstein 'Online!, Beilstein Institut zur Forderung der Chemishchen Wissenschaften, Frankfurt am, XP002267930, Database accession No. BRN 6996995, "substance" and "phamacological data", Imoto, et al., Bull. Chem. Soc. Japan, vol. 59, pp. 3207-3212, 1986.
Database Crossfire Beilstein 'Online!, Beilstein Institut zur Dorderung der Chemishchen Wissenschaften, XP002267931, Database accession No. BRN 8369557, Noguchi, et al., Br. J. Pharacol, vol. 118, No. 4, pp. 941-950, 1996.
Database CA 'Online!, Chemical Abstracts Service, Columbus, Ohio, US, Leopold, et al., Anticancer activity of the structurally novel antibiotic CI-920 and its analogs, XP002267932, retrieved from STN Databse accession No. 101:48172CA, Cancer Research (1984), 44(5), pp. 1928-1932, 1984.
Database CA 'Online!, Chemical Abstracts Service, Columbus, Ohio, US, KOA Corp., Surfactants as pharmaceutical vehicles, retrieved from STN Database accession No. 103:147164 CA (1985).
Database Crossfire Beilstein 'Online! Beilstein Institut zur Forderung der Chemishchen Wissenchaften, Frankfurt am, Main, DE, Jun. 29, 1989, XP002287921, Database accession No. BRN 4043788, BRN 2312546, Deroo, et al., Chem. Phys. Lipids, vol. 16, pp. 60-69, 1976.
Database Crossfire Beilstein 'Online!, Beilstein Institut zur Forderrung der Chemishchen Wissenschaften, Frankfurt am, Main, DE; XP002287922, Database accession No. BRN 6823080; BRN 6819353; BRN 6815243, Overmars, et al., Recl. Trav. Chi, Pays-Bas, vol. 113, No. 5, pp. 293-296, 1994.

(Continued)

*Primary Examiner*—Rebecca Anderson
(74) *Attorney, Agent, or Firm*—Davidson, Davidson & Kappel, LLC

(57) ABSTRACT

The present invention discloses novel phospho-derivatives of branched-chain lipophilic molecules useful for permeabilizing biological barriers and for inhibiting tumor growth. The invention further discloses pharmaceutical compositions comprising said molecules and their uses.

18 Claims, 4 Drawing Sheets

OTHER PUBLICATIONS

Database Chemabs 'Online!, Chemical Abstracts Service, Columbus, Ohio, US, Kurosaki, et al., Purification of phosphate esters or salts, XP002287923, retrieved from STN Database accession No. 106:18824 (1986).

Database Crossfire Beilstein 'Online!, Beilstein Institut zur Forderung der Chemishchen Wissenschaften, Frankfurt am, Main, DE, Mar. 19, 1991, XP002287924, Database accession No. BRN 4049206; BRN 4047939; BRN 4049126; BRN 4049198, Isaacson, et al., J. Biol. Chem., vol. 254, pp. 117-119, 1979.

Database Beilstein 'Online!, Beilstein Institute for Organic Chemistry, Frankfurt-Main, DE, XP002287925, retrieved from Crossfire Database accession No. BRN 1820277, Blake, et al., UN Intern. Corf. Peaceful Uses at Energy, 2, Geneva, vol. 28, pp. 289-293, 1958.

Database Crossfire Beilstein 'Online!, Beilstein Institut zur Forderung der Chemishchen Wissenschaften, Frankfurt am, Main, DE, XP002287926, Database accession No. BRN 1908502. Free acid and derivatives 1-3, Elias, et al., Phosphorus, Sulfur; Silicon Relat. Elem., vol. 85, No. 1-4, pp. 91-100, 1993.

Database Crossfire Beilstein 'Online!, Beilstein Institut zur Forderung der Chemishchen Wissenschaften, Frankfurt am, Main, DE, XP00287927, Database accession No. BRN 2260207, Laskorin, et al., J. Appl. Chem. USSR, vol. 38, pp. 2182-2187, 1965.

Database CA 'Online!, Chemical Abstracts Service, Columbus, Ohio, US, Lion Corp., Hair rinses producing natural luster of the hair, XP002287928, retrieved from STN Database accession No. 95:209360 CA (1984).

Guillod, et al., New anionic glycophospholipids with two perfluorocarbon or two hydrocarbon or mixed hydrophobic chains, Chemistry and Physics of Lipids (1995), 78(2), 149-62, 1995, XP002288367, pp. 149-151.

Database Chemabs 'Online!, Chemical Abstracts Service, Columbus, Ohio, US, Wakatsuki, et al., Phosphate group-containing copolymers, XP002287930, retrieved from STN Database assession No. 107:218259, pp. 4-5, RN 11391-30-1 (1986).

Database Beilstein 'Online!, Beilstein Institute for Organic Chemistry, Frankfurt-Main, DE, Feb. 29, 2000, XP002287935, retrieved from Crossfire Database accession No. BRN 8199592, Romakhin, et al., Russ. J. Gen-Chem., vol. 68, No. 7, pp. 1023-1026, 1998.

Database Beilstein 'Online!, Beilstein Institute for Organic Chemistry, Frankfurt-Main, DE, XP002288369, retrieved from Crossfire, Database accession No. BRN 4040084, Tirri, et al., Lipids, vol. 12, pp. 863, 1977.

Database Beilstein 'Online!, Beilstein Institute for Organic Chemistry, Frankfurt-Main, DE, Jun. 29, 1989, XP002288370, retrieved from Crossfire, Database accession No. BRN 2317987, Fong, et al., Lipids, vol. 12, pp. 857-859, 1977.

Guillod, et al. Synthesis of double tailed (perfluoroalkyl)alkyl phosphosugars, new components for drug-carrying and -targeting systems, Carbohydrate Research, vol. 261, No. 1, pp. 37-55, XP002288368, Aug. 3, 1994.

\* cited by examiner

|  | 30sec | 10min |
|---|---|---|
| FIG. 3A |  |  |
| FIG. 3B |  | 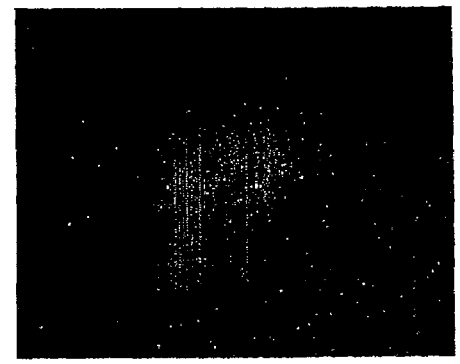 |
| FIG. 3C |  |  |

DERIVATIVES OF BRANCHED-CHAIN LIPOPHILIC MOLECULES AND USES THEREOF

FIELD OF THE INVENTION

The present invention relates to novel phospho-derivatives of branched-chain lipophilic molecules, to pharmaceutical compositions thereof and to use thereof for increasing permeability of biological barriers in a reversible and selective manner and for inhibiting tumor growth.

BACKGROUND OF THE INVENTION

A major limitation in the use of many drugs and therapeutic agents is their inadequate ability to pass through biological barriers. This presents a serious problem especially for the treatment of diseases and disorders in privileged sites such as the central nervous system (CNS).

The blood brain barrier (BBB), made up of specialized microvascular endothelial cells connected by tight junctions, is normally responsible for maintaining the homeostatic environment of the brain and protecting it from toxic agents and degradation products present in the circulatory system. However, in certain pathological situations, the presence of the BBB may interfere with the transport of therapeutic substances into the brain, thus hampering treatment of central nervous system lesions, including tumors, infections, abscesses and degenerative diseases.

In a similar way, the presence of the blood tumor barrier (BTB) interferes with the delivery of chemotherapeutic agents into the tumor, thus decreasing drug bioavailability and preventing efficient therapeutic effect where it is needed. The problem of insufficient access of the therapeutic agent to the diseased target is especially severe in the case of CNS tumors, and patients bearing malignant brain tumors have poor prognoses.

In order to achieve clinically useful concentrations of certain drugs at restricted sites, it is often required to administer these compounds at high systemic dosages. The high systemic concentrations, in turn, are associated with adverse side effects and high levels of toxicity.

One strategy for attacking the problem involves altering the biophysical characteristics of hydrophilic drug molecules, for example, by linking these drugs to a lipophilic carrier. Since drug permeability across such biological membranes depends on its lipophilicity, increasing the lipophilic nature of the compound should, theoretically, improve its bioavailability and increase therapeutic effects. Such covalent polar lipid conjugates with neurologically active compounds for targeting are disclosed in U.S. Pat. No. 5,827,819 to Yatvin et al.

Another approach to circumvent the BBB impermeability is by employing agents that transiently open the BBB and facilitate the entry of a particular drug or agent into the brain. Agents such as mannitol have been shown to exert this desirable effect and have been employed in the delivery of chemotherapeutic agents to malignant brain tumors (Hiesinger et al. (1986), *Annals of Neurology*, 19:50–59). The use of this kind of hyperosmolar BBB disruption in brain tumor therapy has, however, been controversial since, in addition to the drug crossing the BBB, other molecules such as neurotoxins are also permitted entry. This may account for the high incidence of stroke, seizures, immunological reactions and ocular toxicity associated with treatment using osmotic opening methods.

A variety of other treatments have also been disclosed that increase permeability of the blood brain barrier including: the use of bradykinin agonists (WO 91/16355 of Alkermes) and certain other peptides (WO 92/18529 of Alkermes); use of bacterial cell wall fragments (WO 91/16064 of the Rockefeller Univ.) or the use of antibody to *Bordetella pertussis* filamentous haemagglutinin or brain endothelial x-molecule (WO 92/19269 of the Rockefeller Univ.). Certain fatty acids such as oleic acid have also been reported to reversibly open the BBB (Sztriha and Betz (1991), *Brain Res.* 336: 257–262).

The usefulness of methods for reversibly increasing the permeability of the blood brain barrier prior to administration of diagnostic reagents (U.S. Pat. No. 5,059,415 of the Oregon Health Sci. U.) or therapeutic reagents (WO 89/11299 of the Oregon Health Sci. U.) have been disclosed.

It was previously disclosed by the inventors of the present invention, in International patent application publication number WO 99/02120, that branched fatty acids and certain lipophilic derivatives thereof are useful for reversibly permeabilizing biomembranes. However, compounds which comprise a phosphate moiety have not been disclosed. Furthermore, it has not been disclosed that by modifying the branched fatty acids by addition of a phosphate moiety it is possible to modulate the opening of biological barriers in a specific and differential manner.

Clearly, the compositions developed so far for permeabilizing biological membranes and barriers produce severe side-effects. Therefore, there is an unmet need for providing effective and safe means for delivering adequate quantities of therapeutic and diagnostic agents into restricted sites.

Numerous compositions have been proposed for use in treating various cancers, included among them are compounds comprising a hydrocarbon chain and a phosphocholine moiety. U.S. Pat. Nos. 4,837,023 and 5,049,552, both to Eibl, disclose compositions and methods useful in treating cancer. The active material in these cases is the known substance Hexadecylphosphocholine (HePC). However, according to the disclosure in those patents, of all compounds tested only HePC possessed a practically useful anti-tumor action, while homologues with shorter alkyl radicals possessed no or much too low anti-tumor action and homologues with longer alkyl radicals were much too toxic. The prior art neither discloses nor suggests any of the compounds which are the subject matter of the present invention.

SUMMARY OF THE INVENTION

The present invention provides, in one aspect, a compound of the general formula I:

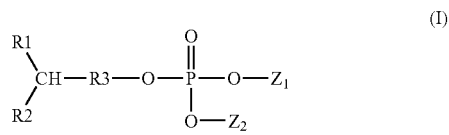

or a pharmaceutically acceptable salt thereof, wherein:

R1 and R2 are the same or different, saturated or unsaturated aliphatic chain comprising from 2 to 30 carbon atoms;

R3 is A-$[CH_2]_m$—B—$[CH_2]_n$—C—$[CH_2]_p$-D wherein m, n and p are each independently zero or an integer from 1 to 12, and A, B, C and D are each independently selected from a covalent bond, amino, amido, oxygen, thio, carbonyl, carboxyl, oxycarbonyl, thiocarbonyl, phosphate, amino phosphate mono- di- and tri-amino phosphate group with the proviso that no two oxygen atoms are directly connected to each other;

$Z_1$ and $Z_2$ are the same or different, each may be absent or independently selected from a) hydrogen, sodium, lithium, potassium, ammonium, mono-, di-, tri- and tetra-alkylammonium, or b) together with the phospho group form a phospho ester of glycerol, choline, ethanolamine, inositol, serine, mono- or oligosaccharide.

In one preferred embodiment, the compound of the general formula I is an α-branched fatty molecule wherein R1 and R2 are hydrocarbon chains having, respectively, 3 and from 12 to 16 carbon atoms.

According to another preferred embodiment, R3 of the compound of the general formula I comprises mono- or di-ethylene glycol moiety.

Currently preferred compounds according to the invention are:

4-Hexadecyl phosphate (3,12-$PO_4$),
4-Octadecyl phosphate (3,14-$PO_4$),
4-Eicosanyl phosphate (3,16-$PO_4$),
8-Pentadecyl phosphate (7,7-$PO_4$),
4-Hexadecanoyloxyethyl phosphate (3,12-MEG-$PO_4$),
2-(4'-Hexadecanoyloxy)ethoxyethyl phosphate (3,12-DEG-$PO_4$),
4-Hexadecanyloxyethyl phosphate (3,12-(ether)-MEG-$PO_4$),
2-(4'-Hexadecanyloxy)ethoxyethyl phosphate (3,12-(ether)-DEG-$PO_4$),
4-Hexadecyl phosphocholine (3,12-PC),
2-(4-Hexadecanoyloxy)ethyl phosphocholine (3,12-MEG-PC),
2-(4-Hexadecanoyloxy)ethoxyethyl phosphocholine (3,12-DEG-PC),
2-{2'-[10"-(Hexadecyl-4-oxy)decyl-1-oxy]ethoxy}ethylphosphate (3,12-O—$C_{10}$-DEG-$PO_4$),
2-{2'-[10"-(Hexadecyl-4-oxy)decyl-1-oxy]ethoxy}ethylphosphocholine (3,12-O—$C_{10}$-DEG-PC),
4-Octadecanoyloxyethyl phosphate (3,14-MEG-$PO_4$),
2-(4'-Octadecanoyloxy)ethoxyethyl phosphate (3,14-DEG-$PO_4$),
4-Octadecanyloxyethyl phosphate (3,14-(ether)-MEG-$PO_4$),
2-(4'-Octadecanyloxy)ethoxyethyl phosphate (3,14-(ether)-DEG-$PO_4$),
4-Octadecyl phosphocholine (3,14-PC),
2-(4-Octadecanoyloxy)ethyl phosphocholine (3,14-MEG-PC),
2-(4-Octadecanoyloxy)ethoxyethyl phosphocholine (3,4-DEG-PC),
4-Eicosanoyloxyethyl phosphate (3,16-MEG-$PO_4$),
2-(4'-Eicosanoyloxy)ethoxyethyl phosphate (3,16-DEG-$PO_4$),
4-Eicosanyloxyethyl phosphate (3,16-(ether)-MEG-$PO_4$),
2-(4'-Eicosanyloxy)ethoxyethyl phosphate (3,16-(ether)-DEG-$PO_4$),
4-Eicosanyl phosphocholine (3,16-PC),
2-(4-Eicosanoyloxy)ethyl phosphocholine (3,16-MEG-PC),
2-(4-Eicosanoyloxy)ethoxyethyl phosphocholine (3,16-DEG-PC),
10-(4'-Hexadecanoyloxy)decanyl phosphate,
10-(8'-Pentadecanoyloxy)decanyl phosphate,
2-[2'-(2"-Propyleicosanoyloxy)-ethoxy]ethyl Phosphate (3,18-DEG-$PO_4$), and
2-(2'-Propyleicosanoyloxy)ethoxy ethylphosphocholine (3,18-DEG-PC).

Currently most preferred compounds are:
2-(4'-Hexadecanoyloxy)ethoxyethyl phosphate, monosodium salt,
2-(4'-Hexadecanoyloxy)ethoxyethyl phosphate, diosodium salt,
2-(4'-Hexadecanyloxy)ethoxyethyl phosphate,
2-(4-Hexadecanoyloxy)ethyl phosphocholine, and
2-(4-Hexadecanoyloxy)ethoxyethyl phosphocholine.

Compounds of the invention are useful for increasing permeability of biological barriers. Thus, in another aspect, the invention provides pharmaceutical compositions comprising an effective amount of a compound of the general formula I depicted above, or a pharmaceutically acceptable salt thereof, and a pharmaceutically acceptable carrier.

The pharmaceutical compositions of the invention may further comprise a pharmaceutically effective amount of a biologically active agent.

In one preferred embodiment, the biologically active agent is a therapeutic agent. The therapeutic agent may be selected from, but is not limited to, anti-tumor, anti-viral anti-microbial, anti-fungal, anti-inflammatory, neuroprotective agents and bioactive peptides and proteins.

In another preferred embodiment, the pharmaceutical compositions of the invention further comprise a diagnostic agent.

The pharmaceutical compositions are useful for facilitating administration of biologically active molecules, for example therapeutic and diagnostic agents, into tissues and organs, in particular at privileged sites which are protected by biological barriers.

In one particular embodiment, the pharmaceutical compositions are useful for increasing drug delivery across the blood retinal barrier (BRB), blood brain barrier (BBB) and blood tumor barrier (BTB). The pharmaceutical compositions, in accordance with the invention, may also be useful for increasing permeability of other biological barriers, thus, for example, facilitating absorption through the skin, cornea, conjunctival, nasal, bronchial, buccal, vaginal and the gastrointestinal epithelium, and across the blood testis barrier and blood kidney interphase.

The pharmaceutical compositions may be administered by oral, parenteral or topical administration or by regional perfusion, enema or intra-organ lavage. Preferably the pharmaceutical compositions of the invention are intra-arterially or intra-thecally administered.

In yet another aspect, the present invention provides methods for increasing permeability of biological barriers. These methods comprise exposing said barriers to an effective amount of a compound of the general formula I, or pharmaceutically acceptable salt thereof, thus enabling or increasing permeability of the biological barrier.

In still another aspect, the present invention provides a method for administration of a biologically active agent into a privileged site or organ comprising exposing said site or organ to said biologically active agent in the presence of an effective amount of a compound in accordance with the invention, thus enabling or increasing the penetration and/or accumulation of the biologically active agent in the privileged site or organ.

The privileged site or organ may be selected from, but is not limited to, the spinal cord, brain, eye, testis, glands and tumors.

In still another aspect, the present invention provides a method for treatment of a tumor comprising administering to a patient in need thereof a therapeutically effective amount of a pharmaceutical composition comprising as an active ingredient a compound of the general formula I in accordance with the invention. Said tumor may be selected from, but not limited to, carcinoma (e.g. breast, colon, rectal and bladder carcinomas), glioma (e.g. astrocytoma), neuroblastoma, retinoblastoma, intraocular malignancy, lymphoma, leukemia, sarcoma and melanoma. The tumor may be a primary or secondary tumor.

The invention further provides a method for treatment of a central nervous system disease or disorder comprising administering to a patient in need thereof a therapeutically effective amount of a pharmaceutical composition comprising a compound of the general formula I, or a pharmaceutically acceptable salt thereof, in combination with a therapeutic agent. The therapeutic agent may be included in the same pharmaceutical composition comprising the compound of the general formula I, or in a separate composition.

In a preferred embodiment the treated disease in the central nervous system is a brain tumor and the therapeutic agent is an anti-cancer drug. In another preferred embodiment the treated disease is an ophthalmologic disease or disorder, for example, cystoids macular edema (CME), Age-related macular degeneration (ARMD), intraocular infections, intraocular inflammations and intraocular malignancies.

In still a further aspect, the present invention provides a method for increasing accumulation of a diagnostic agent in an organ protected by a biological barrier comprising administering to an individual said diagnostic agent in combination with an effective amount of a compound of the general formula I as defied above, thus increasing accumulation of the diagnostic agent in the organ protected by a biological barrier. The diagnostic agent may be included in the same pharmaceutical composition comprising the compound of the general formula I, or in a separate composition.

In one preferred embodiment, said organ protected by a biological barrier is the central nervous system.

BRIEF DESCRIPTION OF THE DRAWINGS

FIGS. 3A–C depict fluorescein sodium salt (F—Na) angiography of the posterior part of a rat eye as recorded at 30 seconds and 10 minutes following administration of F—Na either alone (FIG. 3A), or in combination with 3,12-DEG-HPO$_4$Na (FIG. 3B) or vehicle (FIG. 3C).

DETAILED DESCRIPTION OF THE INVENTION

Figure 1:
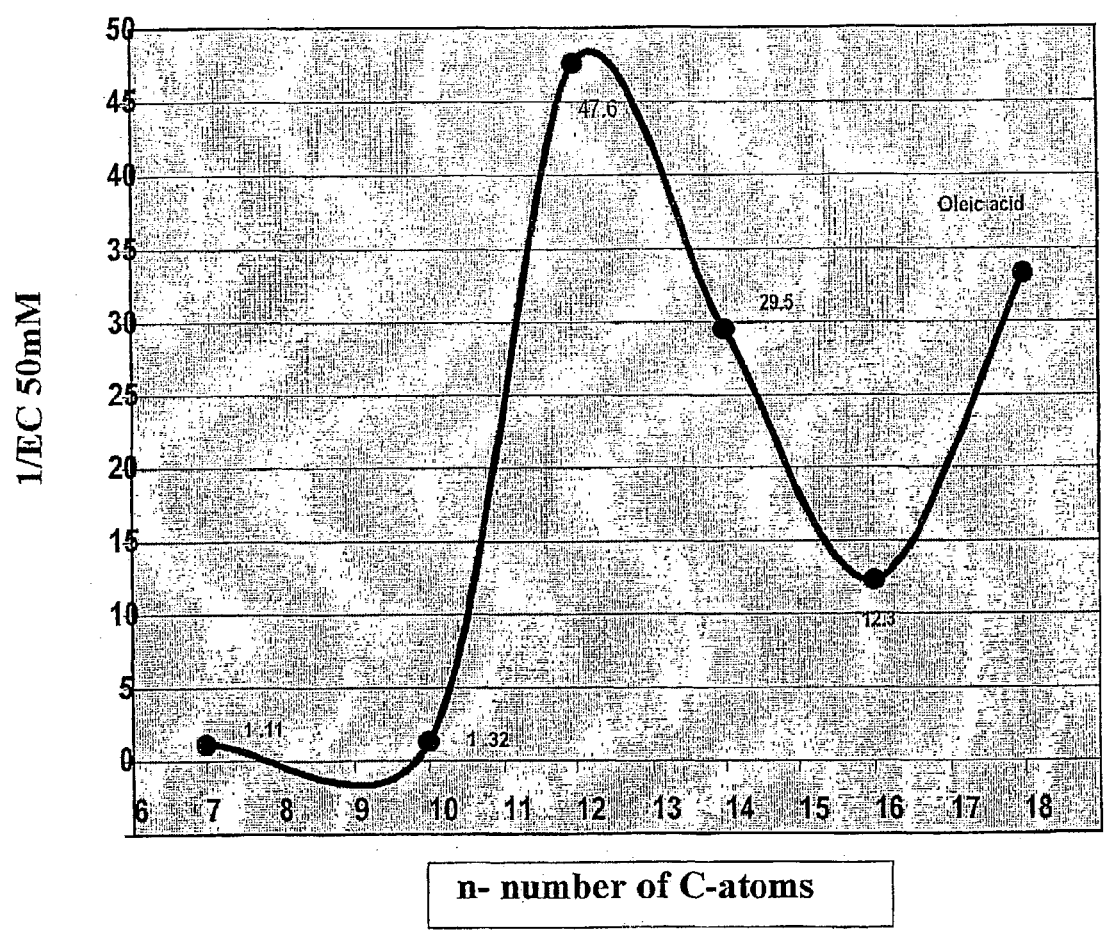
FIG. 1 depicts a graph correlating the various chain lengths of α-branched fatty acids of the 3,n-type, with the potency of these compounds in extravasation of Evans blue-albumin complex into rat brain.

The present invention relates to compounds, compositions and methods for increasing permeability of biological barriers and for inhibiting tumor growth.

A desirable agent for facilitating delivery of therapeutic or diagnostic agents into restricted sites (e.g. the brain, eye, testis etc.) is one that is capable of permeabilizing the limiting biological barrier. However, preferred permeabilization has to be accomplished in a differential fashion without producing unacceptable degree of side effects. For example, in the case of treating a brain tumor, it would be advantageous to use an agent that permeabilizes the BTB to a much greater extent than the BBB in the intact neighbouring brain tissue. Specific permeabilization, in this case, enables preferential accumulation of toxic drugs in the pathological tissue while causing minimal or no damage to the surrounding healthy brain tissue. Similar considerations apply for other biological barriers. For example, it is desirable to have an agent that is capable of increasing delivery of drugs or other beneficial molecules across skin and intestine barriers in a transient and specific fashion.

The present invention concerns novel compounds and is based on the unexpected finding that these compounds may increase permeability of biological barriers in a reversible and selective manner. According to the teaching of the present invention, the novel compounds are of the general formula I as defined hereinabove or pharmaceutically acceptable salts thereof.

In the specification, the compounds of the general formula I will be collectively referred to as "DP-BFAs" or interchangeably by the general name phospho-derivatives of branched chain lipophilic molecules and in short "P-BFA". Branched chain lipophilic molecules not bearing a phosphate moiety will be referred to as "BFA" or "carbo-BFA".

In one preferred embodiment the P-BFAs are phospho-derivatives of α-branched lipophilic molecules of the general structure R1(R2)—CH—. In other embodiments according to the present invention, the P-BFAs are phospho-derivatives of branched lipophilic molecules of the general structure R1(R2)—CH—[CH$_2$]$_m$— wherein m is from 1 to 12, thus referring to ω-branched lipophilic molecules branched, for example, at position β (m=1), γ (m=2) etc.

Specific DP-BFAs will be referred to, hereinafter, by their particular R1 and R2 that represent, respectively, the number of carbon atoms on the side- and main-chain of the branched chain lipophilic molecule.

Compounds of the general formula I, wherein R3 is mono-ethyleneglycol or di-ethyleneglycol will be referred to as R1,R2-MEG-PO$_4$ and R1,R2-DEG-PO$_4$, respectively. In some cases, the bond linking the branched chain moiety and the adjacent chemical group is specifically indicated as, for example, in 3,12-O—C$_{10}$-DEG-PO$_4$, 3,12-(ether)-DEG-PO$_4$ etc. Compounds of the general formula I wherein Z$_1$ is choline will be referred to as R1,R2-PC.

In accordance with the teaching of the present invention, it is possible, by varying the various components in the structure of the compounds of the general formula I, to achieve fine-tuning in stability of the molecules and their permeabilization effect on biological barriers. For example, varying the number of the carbon atoms in the alkyl groups R1 and R2 and the level of saturation affect the overall hydrophobicity of the molecule, thus enabling opimization of its ability to cross specific biological membranes.

Currently preferred compounds in accordance with the invention are DP-BFA molecules wherein the length of the carbon chain in R1 is from 2 to 14, and the total number of carbon atoms in R2 and R3 together is from 6 to 26. Currently more preferred compounds are α-branched chain compounds wherein R1 is 3 carbon atoms and R2 is from 12 to 16 carbon atoms. Preferred compounds of the general formula I comprise an aliphatic chain having up to 20 carbon atoms in length counted from the phosphate group to the branching point of the branched lipophilic molecule. This estimated number of carbon atoms in the R3 moiety of the general formula I as defined above, is most suitable for effective membrane perturbation by the DP-BFA molecule and thus for eliciting of the desirable permeabilization effect. It should be noted that the above-mentioned aliphatic chain may be a continuous hydrocarbon chain, or may be interrupted by one or more heteroatoms selected from the group of oxygen, sulphur, nitrogen and phosphorus atoms, as included in the definition of R3.

In one preferred embodiment in accordance with the invention, R3 of the molecule of the general formula I includes a carbonyl group linking the branched chain moiety and at least one glycol moiety via an ester bond. In another preferred embodiment, R3 includes a covalent bond linking the branched chain moiety and at least one glycol moiety via an ether bond. Under physiological conditions, ether bonds are generally less susceptible to enzymatic cleavage, therefore are expected to be more stable than ester bonds.

Another factor that may affect the ability of DP-BFA compounds to permeabilize various biological barriers is the polarity of the different chemical groups in the molecule. This also may contribute to the fine tuning of the differential permeabilization effect.

Preferred compounds of the invention are in salt forms, being either mono- or di-salt compounds of the general formula I. Suitable salts may include any pharmaceutically acceptable salt comprising a monovalent or divalent counter ion which may be selected from, but is not limited to, $Na^+$, $Li^+$, $K^+$, $NH_4^+$, $Ca^{++}$, $Mg^{++}$, $Mn^{++}$, mono-, di-, tri- and tetra-alkylammonium. More preferred compounds comprise a monovalent salt. Particularly preferred are DP-BFA molecules in the sodium salt form, being either mono- or di-sodium salts.

The compounds of the invention may be prepared by chemical synthetic methods well known in the art. Some of these methods are illustrated hereinafter in the Examples. Alternative procedures known to those skilled in the art may also be employed.

The compounds of the invention were found to be useful in disrupting tight cell junctions in vitro and in increasing permeabilization of biological barriers in vivo. Furthermore, the present invention is based on the unexpected finding that certain derivatives of phospho-branched chain lipophilic molecules have differential effects on opening of the BBB and BTB barriers. Accordingly, the various P-BFA compounds of the invention may be useful in exerting permeabilization of biological barriers while producing minimal toxicity and side effects.

Some DP-BFA compounds are selective in terms of being capable to differentially permeabilizing biological barriers to molecules of different sizes. This characteristic may attribute to higher safety levels of the phospho-BFA agents. Some DP-BFAs differ in the duration of their effect which may be proven as another beneficial factor in certain therapeutic circumstances wherein transient selective permeabilization of a limiting barrier is desirable.

The compounds of the invention and pharmaceutical compositions comprising them may enable or facilitate delivery of biologically active agents across biological barriers.

The term "biologically active agents" is intended to encompass all naturally occurring and synthetic compounds capable of eliciting a biological response, having an effect on biological systems or serving as indicative tools. The biologically active agents may be therapeutic or diagnostic agents.

Therapeutic agents may include, but are not limited to, anti-neoplastic, anti-proliferative, anti-inflammatory, neurological, antibacterial, anti-mycotic and antiviral agents. These compounds in combination with the compounds of the invention are particularly useful in the treatment of pathological conditions, diseases and disorders in restricted sites. For example, in the treatment of central nervous system and lesions including tumors, infections, abscesses and degenerative disorders.

Diagnostic agents may include, but are not limited to, imaging agents, contrast agents and dyes. Examples of diagnostic agents include radioactively labelled substances (e.g. Technetium-99m and Fluoride-18 based agents) and contrast agents such as gadolinium based compounds. The compounds of the invention may be useful, for example, in methods for diagnosing and characterizing brain lesions. In this case, a compound of the invention used for increasing BBB permeability, may be co-introduced (either in the same or separate composition) with a chemical agent that is labelled in such a way that it can be monitored.

The chemical agent to be monitored may be, for example, a general indicator to brain cells or structures, or one that binds or accumulates specifically and exclusively in certain brain areas or brain lesions. The brain, then, may be analyzed to determine the presence of labelling agent. Analysis may be performed using scanning and imaging means known in the art (e.g. magnetic resonance imaging techniques (MRI), positron emission tomography (PET) and Computed Tomography (CT)).

In other embodiments of the invention, the DP-BFA compounds may be useful for enhancement of drug absorption in the intestines or through the skin. The biological barriers in the intestines and skin prevent passive diffusion of a number of substances across the gastrointestinal or skin epithelium thus preventing effective absorption of certain useful chemicals, nutrients and drugs. This obstacle may be overcome by applying the desirable useful chemicals, nutrients and drugs in combination with a DP-BFA compound.

It will be readily apparent to those of ordinary skill in the art that a wide range of biologically active compounds are appropriate for use in combination with the branched lipophilic molecules of the general formula I, therefore are included within the scope of the invention as compounds useful in pharmaceutical compositions or methods of treatment or diagnosis in accordance with the invention. In accordance with the invention, the P-BFA compound is to be administered in combination with the desirable biologically active agent. It should be clarified that the desirable biologically active agent may be included in the same pharmaceutical composition of the compound of the general formula I, or may be administered in a separate composition. Preferably both active agents, i.e. the compound of the general formula I and the desirable biologically active agent(s), are administered simultaneously or within a short period of time from one another. The biologically active agent(s) may be administered prior or, subsequent to the administration of the P-BFA compound, provided that it will be within a time window such that the effect of the P-BFA on the biological barrier is sufficient to facilitate the passage of the relevant agents into the restricted site.

It is also possible that the desirable biologically active agent is not administered around the same time of the P-BFA administration, but is already present in the blood (being either naturally generated in the body or produced as a slow release drug). Some examples include bioactive peptides and proteins such as neurotransmitters, growth factors; hormones, antibodies etc. In this case the requirement is that the permeabilization effect of the target barrier occurs while sufficient amount of the desirable biologically active agent is present to exert its biological effect.

The improved activity of the compounds of the invention in permeabilization of biological barriers results in increased bioavailability of administered drugs, thus extending the therapeutics usefulness of these drugs to conditions that do not respond to lower doses of drugs. This is especially relevant in treatment of diseases and disorders in restricted sites, e.g. brain and the eye.

In addition, the compounds of the invention are advantageous inasmuch as they enable decrease in the useful dosage of drugs and consequently reduction in undesirable systemic side effects. Furthermore, since the molecules of the invention enable selective permeabilization of barriers, they may preferentially increase drug uptake at a specific site (e.g. tumor) and not in the neighboring cells and tissues.

While examining the permeabilization effect of the P-BFA in vivo in tumor-bearing rats, it was surprisingly found that some of the tested compounds showed remarkable cytotoxic effects on the tumor, demonstrated in their ability to significantly inhibit the growth of the treated tumor. Thus, it was established that certain compounds of the invention may be useful as anti-cancer agents. Moreover, some of the compounds of the invention, have demonstrated differential cytotoxic activity when tested for their effect on various normal and tumor cells in vitro.

In accordance with the principles of the present invention, the various DP-BFA molecules may be specifically tailored to suit specific target sites and specific indications. For example, molecules of the invention were found to act in a differential manner in opening the BBB and BTB barriers. In this case the permeabilization of the BTB by certain DP-BFAs is to a greater extent comparing to the effect on the BBB. Another advantageous characteristics of the effect of some DP-BFA molecules, is the preservation of certain levels of discrimination as to the compounds permitted to cross. Thus the DP-BFAs affect barrier permeabilization in a more selective manner comparing to carbo-BFAs or hyperosmotic agents, such as mannitol. As a result, the P-BFA compounds are expected to cause less toxic side effect in comparison to other permeabilizers known in the art. Furthermore, as their permeabilization effect was found to be reversible, the compounds of the invention may also be useful for chronic administration of drugs.

As mentioned in the specification and claims, an "effective amount" of P-BFA refers to that amount of a compound of the invention which exerts the desirable beneficial effect in accordance with the invention. According to one aspect of the invention, it is the amount of P-BFA that significantly increases the permeability of a relevant barrier to a molecule of interest. Namely, the amount of P-BFA which increases the permeability of the relevant barrier to allow sufficient quantities of a molecule of interest to cross the biological barrier so to exert its therapeutic or prophylactic effect or allow diagnostic procedures. According to another aspect of the invention, it is the amount of P-BFA that is therapeutically effective as anti-cancer agent. Namely, that amount of P-BFA which inhibits uncontrolled cell growth.

The effective amount will be determined on an individual basis and will be based, at least in part, on consideration of the individual's size, the specific disease, the severity of the symptoms to be treated, etc. Thus, the effective amount can be readily ascertained by a person of skill in the art employing such factors and using no more than routine experimentation.

The dose range and the regimen employed will be dependent on the route of administration, the age, sex, health and weight of the recipient and on the potency of the particular DP-BFA and the relevant useful drug or agent administered. The skilled artisan will be able to adjust the DP-BFA compositions and dosage in order to obtain the desired duration and the degree of action.

The pharmaceutical compositions may be in a liquid, aerosol or solid dosage form, and may be formulated into any suitable formulation including, but is not limited to, solutions, suspensions, micelles, emulsions, microemulsions, aerosols, ointments, gels, suppositories, capsules, tablets, and the like, as will be required for the appropriate route of administration.

Any suitable route of administration is encompassed by the invention including, but not being limited to, oral, intravenous, intramuscular, subcutaneous, inhalation, intranasal, topical, rectal or other known routes. In preferred embodiments for the permeabilization effect on the CNS, the pharmaceutical composition of the invention is intra-arterially or intra-thecally administered. For use as an anti-cancer medication, the relevant pharmaceutical composition of the invention is preferably administered orally or intravenously or applied topically or by regional perfusion, enema or intra-organ lavage.

The invention will now be illustrated by the following non-limiting examples.

EXAMPLES

I. Chemical Examples

For the sake of clarity, procedures for synthesis of particular P-BFA molecules and salts thereof are exemplified below. However it should be understood that similar procedures are also applicable for synthesis of other P-BFA molecules of the invention including, but not limited to, saturated and unsaturated branched chain molecules and compounds wherein R1 and/or R2 are aliphatic chains comprising a cyclic alkyl group(s). Various pharmaceutically acceptable salts of the P-BFA molecules could also be obtained including, but not limited to, sodium, potassium, ammonium and alkyl-ammonium salts and salts with divalent counter-ions.

All synthesized compounds were characterized by NMR, mass spectroscopy and element analyses.

Example 1

Synthesis of Alkyl Phosphates

Phosphates of the general formula RO—P(O)(OH)$_2$ were prepared. R represents a branched-chain alkyl moiety of the R$_1$(R$_2$)—CH structure where R$_1$ indicates the number of carbons in the side alkyl chain and R$_2$ indicates the number of carbons in the main alkyl chain.

The synthesis of RO—P(O)(OH)$_2$ molecules is a three-stage procedure. In the first stage the corresponding alcohol (R—OH) was prepared from aldehyde and alkyl bromide using the Grignard reaction (Vogel's, "Textbook of practical organic chemistry", Wiley, New York, pg. 531, (1996).)

In the second stage diphenyl phosphate ester was prepared from the alcohol and diphenyl phospochloridate:

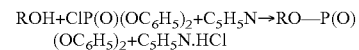

In the third stage alkanyl dihydrogen phosphate was obtained by hydrogenation of the diphenyl ester.

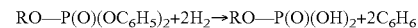

4-Hexadecanyl Diphenyl Phosphate.

Diphenyl phosphorochloridate (4.0 g, 0.015 mole) was added slowly while shaking to a solution of hexadecane-4-ol (2.4 g, 0.01 mole) in dry pyridine (5 ml) at room temperature. The flask was stoppered and set aside for 48 hr.; then the contents were poured into ice-cold 1N hydrochloric acid (100 ml). The heavy oil, which separated was extracted with ether. The ethereal layer was washed with 1N hydrochloric acid (3 times), 5% sodium hydrogen carbonate (5 times), and water (5 times). After being dried ($MgSO_4$), the ether was removed, and the residue was purified by column chromatography (Petrol Ether (bp 30–60° C.): Ether, 10:1). After evaporation of a solvent 3.5 g of liquid was obtained. Yield 74%.

4-Hexadecanyl Phosphate. (3,12-$PO_4$)

A suspension of platinum oxide (Adams catalyst) (0.32 g) in glacial acetic acid (20 ml) was shaken under hydrogen atmosphere until absorption ceased. The Adams catalyst was then washed well with 2N hydrochloric acid, water, and finally glacial acetic acid, by decantation. Solution of 4-Hexadecanyl diphenyl phosphate (3.2 g) in glacial acetic acid (40 ml) was added to the catalyst, and the solution was shaken under hydrogen until absorption ceased. The catalyst was filtered off and washed with chloroform. The solvents were removed from the filtrate in vacuo. The residue was crystallized from petroleum ether (bp 30–60° C.) and dried at 65° C. 2.01 g of final product was obtained. Yield 92%.

4-Hexadecanyl Disodium Phosphate. (3,12-$PO_4Na_2$)

4-Hexadecanyl phosphate (1 g, 0.0031 mol) was dissolved in ethanol (100 ml). NaOH (0.25 g, 0.0062 mol) was added and the mixture was stirred for 1 hr. and then evaporated. Ethanol (2×100 ml) was added and evaporated. Ether (100 ml) was added and evaporated. The residue was crystallized from acetone (30 ml) and dried at 65° C. (15 mm. Hg). 0.9 g of final product was obtained. Yield 79%.

$^1$H-NMR ($CD_3OD$): δ 0.89 (m, 6H), 1.27 (s, 22H), 1.58 (m, 4H), 4.22 (m, 1H). MS (FAB): m/z 367.06 $(M+H)^+$.

4-Hexadecanyl Monosodium Phosphate. (3,12-$HPO_4Na$)

4-Hexadecanyl phosphate (3.13 g, 0.0097 mol) was dissolved in ethanol (150 ml). NaOH (0.37 g, 0.0092 mol) was added and the mixture was stirred for 48 hrs and then evaporated. Ethanol (2×150 ml) was added and evaporated. Ether (2×100 ml) was added and evaporated. The obtained solid was triturated with acetone (100 ml) and dried under 1 mm. Hg atmosphere overnight. 2.98 g of final product was obtained. Yield 87%.

$^1$H-NMR ($CD_3OD$): δ 0.87 (m, 6H), 1.25 (s, 22H), 1.51 (m, 4H), 4.12 (m, 1H). MS (FAB): m/z 345.11 $(M+H)^+$.

4-Octadecanyl Disodium Phosphate. (3,14-$PO_4Na_2$)

$^1$H-NMR ($CD_3OD$): δ 0.89 (m, 6H), 1.27 (s, 26H), 1.58 (m, 4H), 4.17 (m, 1H). MS (FAB): m/z 395.20 $(M+H)^+$.

4-Octadecanyl Monosodium Phosphate. (3,14-$HPO_4Na$)

$^1$H-NMR ($CD_3OD$): δ 0.90 (m, 6H), 1.28 (s, 26H), 1.56 (m, 4H), 4.14 (m, 1H). MS (FAB): m/z 373.29 $(M+H)^+$.

8-Pentadecanyl Disodium Phosphate. (7,7-$PO_4Na_2$)

$^1$H-NMR ($CD_3OD$): δ 0.90 (m, 6H), 1.30 (s, 20H), 1.60 (m, 4H), 4.12 (m, 1H). MS (FAB): m/z 352.93 $(M+H)^+$.

8-Pentadecanyl Monosodium Phosphate. (7,7-$HPO_4Na$)

$^1$H-NMR ($CD_3OD$): δ 0.90 (m, 6H), 1.30 (s, 20H), 1.60 (m, 4H), 4.12 (m, 1H). MS (FAB): m/z 353.05 $(M+Na)^+$.

Example 2

Synthesis of 2-(2'-Propyltetradecanoyloxy)ethyl Phosphate

This compound was prepared by the same procedures as described above in Example 1 using the alcohol: $C_3H_7$—C($C_{12}H_{25}$)H—C(O)—O—$CH_2$—$CH_2$—O—. This alcohol was obtained from chloride anhydride of 2-Propyl pentanoic acid and ethylene glycol (Vogel's, "Textbook of practical organic chemistry", Wiley, New York, pg. 698, (1996)).

2-(2'-Propyltetradecanoyloxy)ethyl Disodium Phosphate (3,12-MEG-$PO_4Na_2$)

$^1$H-NMR ($CDCl_3$): δ 0.87 (m, 6H), 1.24 (s, 22H), 1.54 (m, 4H), 2.33 (m, 1H). 3.87 (m, 2H), 4.26 (m, 2H). MS (FAB): m/z 439.19 $(M+H)^+$.

2-(2'-Propyltetradecanoyloxy)ethyl Monosodium Phosphate (3,12-MEG-$HPO_4Na$)

$^1$H-NMR ($CDCl_3$): δ 0.87 (t, 6H), 1.24 (s, 20H), 1.42 (m, 2H), 1.56 (m, 2H), 2.34 (m, 1H). 4.02 (m, 2H), 4.28 (m, 2H). MS (FAB): m/z 417.19$(M+H)^+$.

Example 3

Synthesis of 2-[2'-(2"-Propyltetradecanoyloxy)-ethoxy]ethyl Phosphate

This compound was prepared by the same procedures as described above in Example 1 using the alcohol: $C_3H_7$—C($C_{12}H_{25}$)H—C(O)—O—$CH_2$—$CH_2$—O—$CH_2$—$CH_2$—O—. This alcohol was obtained from chloride anhydride of 2-Propyl pentanoic acid and diethylene glycol (Vogel's, "Textbook of practical organic chemistry", Wiley, New York, pg. 698, (1996)).

2-[2'-(2"-Propyltetradecanoyloxy)-ethoxy]ethyl Disodium Phosphate (3,12-DEG-$PO_4Na_2$)

$^1$H-NMR ($CD_3OD$): δ 0.90 (m, 6H), 1.30 (s, 20H), 1.44 (m, 2H), 1.59 (m, 2H) 2.39 (m, 1H). 3.72 (m, 4H), 4.09 (m, 2H), 4.24 (m, 2H). MS (FAB): m/z 483.03 $(M+H)^+$

2-[2'-(2"-Propyltetradecanoyloxy)-ethoxy]ethyl Monosodium Phosphate (3,12-DEG-$HPO_4Na$)

$^1$H-NMR ($CD_3OD$): δ 0.90 (m, 6H), 1.30 (s, 20H), 1.44 (m, 2H), 1.59 (m, 2H) 2.39 (m, 1H). 3.72 (m, 4H), 4.09 (m, 2H), 4.24 (m, 2H). MS (FAB): m/z 461.31 $(M+H)^+$.

Additional compounds were prepared in an analogous way. For Example, the compound 2-[2'-(2"-Propyleicosanoyloxy)-ethoxy]ethyl Phosphate was prepared by using the alcohol: $C_3H_7$—C($C_{18}H_{37}$)H—C(O)—O—$CH_2$—$CH_2$—O—$CH_2$—$CH_2$—O—. This alcohol was obtained from chloride anhydride of 2-Propyl eicosanoic acid and diethylene glycol.

2-[2'-(2"-Propyleicosanoyloxy)-ethoxy]ethyl Monosodium Phosphate (3,18-DEG-$HPO_4Na$)

$^1$H-NMR ($CD_3OD$): δ 0.90 (m, 6H), 1.30 (s, 34H), 1.44 (m, 2H), 1.59 (m, 2H) 2.39 (m, 1H). 3.72 (m, 4H), 4.09 (m, 2H), 4.24 (m, 2H). MS (FAB): m/z 544.31 $(M+H)^+$.

Example 4

Synthesis of 2-{2'-[10"-(Hexadecyl-4-oxy)decyl-1-oxy]ethoxy}ethylphosphate monosodium salt (3,12-O—$C_{10}$-DEG-$HPO_4Na$)

This compound was prepared by the same procedures as described above in Example 1 using the alcohol: $C_3H_7$—C($C_{12}H_{25}$)H—O—$(CH_2)_{10}$—O—$CH_2CH_2$—$CH_2$—OH—. This alcohol was obtained in a two-step procedure: First, reacting 4-Hexadecanol tosylate (Vogel's, "Textbook of practical organic chemistry", Wiley, New York, pg. 698, (1996)) with monosodium 1,10-decanediole to generate 10-(Hexadecyl-4-oxy)decanol. At a second step, the alcohol 2'-[10"-(Hexadecyl-4-oxy]decyl-ethyloxyethanol was prepared by reacting 10-(Hexadecyl-4-oxy)decanol tosylate (generated as in step 1) with sodium 2-(2-hydroxyethyloxy) ethylate.

$^1$H-NMR (CD$_3$OD): δ 0.90 (m, 6H), 1.30 (s, 38H), 1.44 (m, 2H), 1.59 (m, 2H) 3.15 (m, 1H). 3.37 (m, 4H), 3.45–3.62 (6H), 3.95(m, 2H). MS (FAB): m/z 565.45 (M+H)$^+$.

Example 5

Synthesis of 2(4-Hexadecanoxy)ethoxyethyl Phosphate

This compound was prepared by the same procedures as described above in Example 1 using the alcohol: C$_3$H$_7$—C(C$_{12}$H$_{25}$)H—O—CH$_2$—CH$_2$—O—CH$_2$—CH$_2$—O—. This alcohol was obtained from sodium 2-(2-hydroxyethyloxy) ethylate and 4-Hexadecanol tosylate. (Vogel's, "Textbook of practical organic chemistry", Wiley, New York, pg. 698, (1996)).

4-Hexadecanesulfonyl chloride.

4-Hexadecanol (12.29 g 0.051 mol) and p-Toluenesulfonyl chloride (12 g 0.063 mol) were dissolved Pyridine (100 ml) and stirred overnight at room temperature. Dichloromethane (400 ml) was added. Dichloromethane solution was then washed well with water, H$_2$SO$_4$ (3%), water, NaHCO$_3$ (3%) and water, dried with anhydrous magnesium sulphate (10 g). After evaporation of the solvent 20 g of crude 4-Hexadecanesulfonyl chloride was obtained.

2(4-Hexadecanoxy)ethoxyethanesulfonyl chloride.

Sodium (3.5 g 0.15 mol) was added to Di(ethylene glycol) (140 ml 1.5 mol) at 60° C. in small pieces. To obtained solution 4-Hexadecanol tosylate (crude 20 g) in THF (300 ml) was added at same temperature. Solution was stirred at reflux for 6 hrs. Water (100 ml) was added to the mixture at room temperature. The mixture was extracted with ethyl acetate (300 ml). After evaporation of the solvent the residue was purified by column chromatography (Petrol Ether (bp 30–60° C.): Ether, 1:1). 4 g of 2(4-Hexadecanoyl) ethoxyethyl was obtained. Yield 24% starting from 4-Hexadecanol.

2(4-Hexadecanoxy)ethoxyethyl Disodium Phosphate (3,12-ether-DEG-PO$_4$Na$_2$)

$^1$H-NMR (CD$_3$OD): δ 0.9 (m, 6H), 1.28 (s, 22H), 1.43 (m, 4H), 3.30 (m, 1H), 3.60 (m, 4H), 3.69 (m, 2H), 4.07 (m, 2H). MS (FAB): m/z 455.45(M+H)$^+$.

Example 6

Synthesis of 2-(2'-Propyltetradecanoyloxy)ethoxyethylphosphocholine.

Phosphocholine of the formula C$_3$H$_7$—C(C$_{12}$H$_{25}$)H—C(O)—O—CH$_2$—C$_2$H$_2$—O—CH$_2$—CH$_2$—O—PO$^-$(O)—O—CH$_2$CH$_2$N$^+$(CH$_3$)$_3$ was prepared as follows:

2-(2'-Propyltetradecanoyloxy)ethoxyethylphosphocholine (3,12-DEG-PC)

To a cooled solution (0° C.) of 2-(2'-propyltetradecanoyloxy)ethoxyethanol (15.8 g, 0.044 mol) and triethylamine (10 ml, 0.075 mol) in dry ether (250 ml) was added 2-chloro-2-oxo-1,3,2-dioxaphospholane (7 ml, 0.075 mol) in 200 ml of dry ether. The mixture was stirred at room temperature for 2 hrs. The crystalline (C$_2$H$_5$)$_3$N.HCl that precipitated was filtered off, and the solvent was removed in vacuum. The residue was dissolved in 500 ml solution of trimethylamine (0.27M) in anhydrous acetonitrile and transferred to a pressure bottle. The pressure bottle was kept for 48 hrs in an oil bath at 60–65° C. The bottle was then cooled and opened. The solvent was removed, and the residue was purified by column chromatography (CHCl$_3$:CH$_3$OH:H$_2$O, 1:9:1). The oil obtained after evaporation of the solvent was lyophilized during 72 hrs at 65° C. 17.4 g of slight yellow wax was obtained. Yield 75%.

$^1$H-NMR (CD$_3$OD): δ 0.9 (t, 6H), 1.29 (s, 22H), 1.46 (m, 2H), 1.59 (m, 2H), 2.38 (m, 1H), 3.25 (S, 9H), 3.69 (m, 6H), 3.99 (m, 2H), 4.29 (m, 4H). MS (FAB): m/z 524.6 (M+H)$^+$.

The following compounds were synthesized by a process analogous to the above-described procedure.

2-(2'-Propyleicosanoyloxy)ethoxyethylphosphocholine (3,18-DEG-PC)

$^1$H-NMR (CD$_3$OD): δ 0.9 (t, 6H), 1.29 (s, 34H), 1.46 (m, 2H), 1.59 (m, 2H), 2.38 (m, 1H), 3.25 (S, 9H), 3.69 (m, 6H), 3.99 (m, 2H), 4.29 (m, 4H). MS (FAB): m/z 608.6 (M+H)$^+$.

2-{2'-[10"-(Hexadecyl-4-oxy)decyl-1-oxy]ethoxy}ethylphosphocholine (3,12-O—C$_{10}$-DEG-PC)

$^1$H-NMR (CD$_3$OD): δ 0.9 (t, 6H), 1.29 (s, 34H), 1.46 (m, 2H), 1.59 (m, 2H), 2.38 (m, 1H), 3.25 (S, 9H), 3.69 (m, 6H), 3.99 (m, 2H), 4.29 (m, 4H). MS (FAB): m/z 608.6 (M+H)$^+$.

Example 7

Synthesis of 2-(2'-Propyltetradecanoyloxy)ethylphosphocholine

Phosphocholine of the formula C$_3$H$_7$—C(C$_{12}$H$_{25}$)H—C(O)—O—CH$_2$—CH$_2$—O—PO$^-$(O)—O—CH$_2$CH$_2$N$^+$(CH$_3$)$_3$ was prepared by the same procedure as described above in Example 6, except that the corresponding alcohol, i.e. 2-(2'-propyltetradecanoyloxy)ethanol, was used instead of 2-(2'-propyltetradecanoyloxy)ethoxyethanol.

2-(2'-Propyltetradecanoyloxy)ethylphosphocholine (3,12-MEG-PC)

$^1$H-NMR (CD$_3$OD): δ 0.9 (t, 6H), 1.29 (s, 22H), 1.46 (m, 2H), 1.59 (m, 2H), 2.39 (m, 1H), 3.24 (S, 9H), 3.66 (m, 2H), 4.07 (m, 2H), 4.28 (m, 4H). MS (FAB): m/z 480.7 (M+H)$^+$.

Example 8

Synthesis of Alkylphosphocholines.

Phosphocholine compounds of the formula RO—PO(O)—O—CH$_{2CH2}$N$^+$(CH$_3$)$_3$ were prepared by the same procedure as described above in Example 6, except that R—OH was used as the alcohol in the initial step. R represents branched chain alkyls of the R$_1$—C(R$_2$)H-type.

4-Hexadecanyl phosphocholine (3,12-PC)

$^1$H-NMR (CD$_3$OD): δ 0.91 (t, 6H), 1.28 (s, 22H), 1.57 (m, 4H), 3.21 (S, 9H), 3.62 (m, 2H), 4.25 (m, 3H). MS (FAB): m/z 408.68 (M+H)$^+$.

4-Octadecanyl phosphocholine (3,14-PC)

$^1$H-NMR (CD$_3$OD): δ 0.9 (t, 6H), 1.28 (s, 26H), 1.57 (m, 4H), 3.21 (S, 9H), 3.61 (m, 2H), 4.23 (m, 3H). MS (FAB): m/z 436.91 (M+H)$^+$.

8-Pentadecanyl phosphocholine (7,7-PC)

$^1$H-NMR (CD$_3$OD): δ 0.92 (t, 6H), 1.32 (s, 20H), 1.59 (m, 4H), 3.23 (S, 9H), 3.63 (m, 2H), 4.26 (m, 3H). MS (FAB): m/z 394.35 (M+H)$^+$.

Example 9

Synthesis of ω-branched P-BFA

ω-branched P-BFA compounds are prepared by the same procedures described above in Examples 1 and 6 using the relevant ω-alcohols.

The preparation of ω-branched BFA is a six-stage synthesis. The starting reagents are 1-Bromo-ω-alcohol and n-Alkyl-m-alkylketone.

The first stage is protection of the hydroxyl group of 1-Bromo-ω-alcohol by Dihydropyran (DHP) following the procedure as described by Kocienski ("Protecting Group"; Georg. Thieme Verlag Stuttgart. N-Y. pg. 83–84 (1994)).

Stage 1:

$$Br(CH_2)_\omega OH + DHP \rightarrow \qquad\qquad I$$

$$Br(CH_2)_\omega OTHP \qquad\qquad II$$

THP denotes a Tetrahydropyranyl ether.

The second and third stages are standard Grignard synthesis of tertiary alcohol (Vogel's, "Textbook of practical organic chemistry", Wiley, New York, pgs. 475, 538, (1996)) as follows.

Stage 2:

$$Mg + Br(CH_2)_\omega OTHP \rightarrow BrMg(CH_2)_\omega OTHP \qquad\qquad III$$

Stage 3:

$$BrMg(CH_2)_\omega OTHP + RR'-CO \rightarrow RR'C(OH)-(CH_2)_\omega OTHP \qquad\qquad IV$$

R,R'-denote alkyl groups.

The fourth stage is reduction of tertiary hydroxy group of compound (IV) by ionic hydrogenation reaction following the procedure as described by Carey and Tremper. (JACS, v. 91, p. 2967, (1969))

Stage 4:

$$RR'C(OH)-(CH_2)_\omega OTHP + SiHEt_3 \rightarrow RR'CH(CH_2)_\omega OTHP \qquad\qquad V$$

The fifth stage is cleavage of the protection group off the obtained ω-branched alcohol (V) ("Protecting Group"; Georg. Thieme Verlag Stuttgart. N-Y. pg. 83–84 (1994)).

The final stage, stage 6, is oxidation of the ω-branched alcohol to the corresponded ω-branched BFA. This was carried out following the procedure as described by Manger and Lee (Tetraehedron letters, v.22, N.18, p.1655, (1981)).

Stage 6:

$$RR'CH(CH_2)_\omega OH + [O] \rightarrow RR'CH(CH_2)_\omega COOH$$

II. Physico-Chemical Properties

Example 10

In Vitro Lipophilicity Measurements of DP-BFAs

The lipophilicity values of various derivatives of branched fatty acids were estimated by comparing the solubility of these compounds in organic versus aqueous solutions. Octanol and physiological saline were used, respectively, as the organic and aqueous solutions. The partition coefficient ($P_c$) value, i.e. the octanol/saline distribution was measured by the shake-flask technique. The results, i.e. mg/ml solubility in octanol and water and the calculated $LogP_c$, are shown in Table 1.

TABLE 1

Octanol-saline partition coefficients ($P_c$)

| Molecule* | Octanol mg/ml | Water mg/ml | $LogP_c$ |
|---|---|---|---|
| 7,7 | >50 | >25 | 1.33 |
| 3,12 | >20 | >10 | 0.99 |
| 3,14 | >20 | >10 | 1.26 |
| 3,16 | >20 | 9.4 | 1.26 |
| 7,7-PO$_4$ | >10 | >10 | <5 |
| 3,12-PO$_4$ | <5 | >2.5 | 1.9 |
| 3,14-PO$_4$ | >10 | <0.5 | 1.11 |
| 3,12-MEG-PO$_4$ | >10 | >10 | 1.09 |
| 3,12-DEG-PO$_4$ | >5 | 8 | 1.31 |
| 3,12-(ether)-DEG-PO$_4$ | >5 | >5 | 0.83 |
| 3,12-PC | >10 | >10 | |
| 3,12-MEG-PC | >10 | >10 | 1.22 |
| 3,12-DEG-PC | >50 | >10 | 0.73 |

*sodium salts of the branched fatty acids and their PO$_4$ derivatives

Example 11

Structure-Function Correlations

In this study a correlation between the physico-chemical properties of the branched chain molecules and their biological effects was assessed. The study was aimed to find out whether there is a correlation between the chain length of branched chain molecules and their potencies in Evans blue (EB) extravasation in rat brain (see Example 18 for the procedure used in measuring $EC_{50}$ values). Various branched fatty acids of the 3,n-type, wherein one branched chain is of 3 carbon atoms and the second hydrocarbon chain, n, is from 7 to 16 carbon atoms, were used. The results are graphically depicted in FIG. 1.

As can be seen in FIG. 1, BFAs 3,12, 3,14 and 3,16 were found to be active in permeabilization of the BBB. Under the experimental conditions employed, the most potent compound among the tested molecules is BFA-3,12.

III. Biological Examples

III-a) In Vitro Studies

Example 12

Comparative In Vitro Toxicity Study

Various DP-BFA molecules were screened in cultured Chinese hamster ovary (CHO) AA8 cell line in order to establish their toxicity. $LC_{50}$ values, i.e. the concentrations causing death in 50% of cell population, were calculated from dose response curves. $LC_{50}$ values of phospho-BFAs were compared to those of the corresponding branched fatty acids (=carbo-BFAs).

Method

Lactate dehydrogenase (LDH) release was used as an assay for the integrity of the cells membrane and, thus, for estimation of toxicity. Cells ($2\times10^5$/ml) were seeded (150 μl/well) in 96 well plates, in RPMI-1640 medium containing 10% FCS. After two days, tested DP-BFA compounds or the control compound myristic acid were added to the plates in declining concentrations ranging from 500 to 1 μg/ml. Cells were harvested after one hour. Forty-five minutes before harvesting, 16.5 μl of lysis solution was added to the first 6 wells in order to demonstrate complete lysis and maximum lactate dehydrogenase release which indicate cell death. Other controls included, two blank wells and five wells containing cells with no additional drugs. Following centrifugation (1500 rpm, 5 min), 75 µl of the supernatant was transferred to a new plate with 45 µl of an LDH assay mix (Tox-7 kit, Sigma). After 10–20 minutes at room temperature, absorbance was measured using an Elisa Reader 490 nm.

Toxicity data obtained following 1 hour incubation with different DP-BFAs is summarized in Table 2. Each experiment was performed in triplicate.

TABLE 2

Toxicity of BFAs and their phospho-derivatives on cell cultures

| Tested compound | $LC_{50}$ (µM) |
| --- | --- |
| 7,7-Na | 65 |
| 7,7-$PO_4Na_2$ | 320 |
| 3,12-Na | 165 |
| 3,12-$PO_4Na_2$ | 320 |
| 3,12-DEG-$PO_4Na_2$ | 320 |

In general, the cells were found to be more sensitive to carbo-BFA and less sensitive to the tested phospo-BFA derivatives. Sub-toxic doses for carbo-BFA were estimated at between 30–100 µM following incubation for 1 hour. Under the same conditions, sub-toxic doses for the tested phospho-BFA derivatives were estimated to range from 160 µM to more than 640 µM.

Conclusion: In general, the phospho-BFAs were found to be around 2 to 5 times less toxic than the corresponding carbo-BFAs molecules.

Example 13

Effects of DP-BFA on Epithelial Cell Junctions

Effects of the various BFA derivatives on cell-cell junctions were investigated using the human adenocarcinoma cell line (A431). These cells have a polarized structure characteristic of intestinal cells.

In this study, quantitative changes in the subcellular distribution of $ZO_2$, a protein associated with tight junction complexes (Anderson et al. (1993) *Current Opinion in Cell Biology* 5: 772–778) was monitored.

A431 cells, cultured in DMEM with serum on glass cover-slips, were incubated for one hour in the presence or absence of sub-toxic doses of DP-BFA. The cells were fixed and permeabilized for 2 minutes with a mixture of 3% paraformaldehyde and 0.5% Triton-X-100, and then further fixed for 20 min with 3% paraformaldehyde alone. The fixed cells were rinsed and incubated for 45 minutes at room temperature with rabbit polyclonal antibody $ZO_2$ (Zymed Laboratories, Inc. USA), washed 3 times with PBS and incubated for 45 min with fluorescently labelled secondary antibodies. Stained cover-slips were mounted in Elvanol (Mowiol 4-88, Hoechst, Frankfurt, Germany) before microscopic examination. The distribution of the immuno-fluorescently labelled $ZO_2$ protein was monitored.

A431 cells that were incubated for one hour with pervanadate, which inhibits phosphotyrosine phosphatases and thus disrupts cell junctions, were used as a positive control.

The fluorescent imaging of $ZO_2$ indicated that DP-BFA has clear effects on disruption tight junctions of A431 cells.

Example 14

Effects of DP-BFA on Permeability of Epithelial Cell Monolayer

The aim of this study was to assess the kinetics and overall effect of the DP-BFA compounds in modifying the permeability of an epithelial cell monolayer, which served as an in vitro model system for biological barriers and particularly for the intestinal barrier.

Two approaches were taken in order to determine the effect of DP-BFA on permeabilization of biological barriers. One approach was to follow transport of a radioactive labelled compound across the epithelial cell monolayer. A second approach was to monitor changes in electrical resistance as a measurement indicating the permeability level of the cell layer.

Epithelial cells are cultured on a membrane filter (0.4 micron, 1 $cm^2$). The membrane with the epithelial cell monolayer is placed between two compartments, a donor and a receiver chamber. The tested P-BFA compound, at predetermined non-toxic concentration, and $^{14}C$-sucrose radioactive tracer (1 Ci in 0.5 ml buffer) are added to the apical (donor) side. Samples of 0.5 ml each are collected from the basolaeral (receiver) side at 10 minutes intervals for the 90 minutes duration of the experiment. Incubation is carried out in tissue culture medium containing 1% FCS while shaking at 70 rpm. The apical chamber and membrane are transferred into a new receiver chamber at each sampling time point. This is done in order to keep constant concentration of the tracer in the apical chamber and invariable liquid volumes in both chambers. The concentration of radioactive tracer in the collected samples are estimated using a Trilux microbeta counter (Wallac, Finland). The rate of tracer transport is calculated and expressed as Permeability Coefficient.

Integrity of the epithelial monolayer used in the experiment is monitored at the beginning and end of incubation by measuring the trans-epithelial electrical resistance (TEER) using millicell-ERC (Millipore).

A parallel set of experiments is conducted using the same experimental system as described above but without the addition of the radioactive tracer. Trans-epithelial electrical resistance (TEER) was monitored every 10 minutes for a period of 90 minutes.

Conclusion: the fact that i) P-BFAs significantly increase the passage of sucrose across the epithelial cell monolayer, and ii) decrease the TEER of the monolayer, support the conclusion that P-BFA compounds permeabilize biological barrier.

Example 15

Cytotoxic Activity of Various DP-BFAs on Normal and Malignant Cell Types

The cytotoxic activity of various phospho-derivatives of branched-chain fatty acids (DP-BFAs) was assayed in vitro in cell cultures that include normal and malignant cell types. The following cell systems were used:

Primary fibroblasts (human)

Normal bone marrow (BM) cells (mouse)

Primary bronchial epithelial cells (human, from Clonetics, cat. no. CC-2541)

Caco-2—colon cancer cell line (human, ATTC, HTB-37)
C6 glioma cell line (rat, ATCC, CRL-2199)
Neuro2a—neuroblastoma cell line (mouse, ATCC, CCL-131)
SKBR-3—breast cancer cell line (human, ATTC, HTB-30)
HL60—myeloid leukemia cell line (human, ATCC, CCL-240)
U937—myeloid leukemia cell line (human)

Cells were seeded in a microtiter plate in MEM containing 2 mM L-glutamine, 100 units/ml penicillin, 100 ug/ml streptomycin and 10% FCS at 37° C. The cultured cells were incubated, during their linear growth phase in the absence (control group) or presence of various DP-BFAs as indicated. The final concentrations of the tested DP-BFAs ranged from 1.5 to 200 microMolars. At the end of the incubation period, which was five days for the bone marrow cells and three days for all the other cell lines, the cytotoxic effect of the added P-BFA on the cells was estimated by using the colorimetric MTT assay. The MTT assay (Mosmann (1983) J. Immunol Methods 65: 55–63) measures mitochondrial reductase activity and serves for quantitative assessment of cellular viability. Drug concentration that causes 50% reduction in cell viability in comparison to the control group, is defined as $EC_{50}$. The $EC_{50}$ values of the tested DP-BFA compounds were calculated from dose response curves established for each of the different assayed cell lines.

The results are summarized in Table 3. Each $EC_{50}$ value is an average of $EC_{50}$ values derived from 1–5 independent experiments.

As can be seen from the results in Table 3, the various DP-BFAs molecules were active to a different degree in their cytotoxic effect on the different cells. Among the tested compounds, the most potent cytotoxic agents for malignant cells were 3,12-DEG-PO$_4$, 3,12-(ether)-DEG-PO$_4$, 3,12-MEG-PC, 3,12-DEG-PC, 3,18-DEG-PC and 3,14-PC. Two of these compounds, 3,12-DEG-PO$_4$ and 3,12-(ether)-DEG-PO$_4$, were found to have the lowest cytotoxic activity on normal epithelial cells. Another compound, 3,12-DEG-PC, was found to have the lowest cytotoxic activity on normal fibroblasts and normal bone marrow cells.

Conclusions: Phospho-BFA compounds have demonstrated cell-type specific cytotoxic effects. Few of these compounds were shown as most potent cytotoxic agents when tested on malignant cell lines, while being much less toxic when tested on normal cells from different tissues. These data suggest that these compounds may be efficient anti-cancer agents with low cytotoxic side effects.

Example 16

3,12-DEG-PC Induces Activation of Caspase-3 and DNA Fragmentation in a Neuroblastoma Cell Line In order to further explore the possible mechanism underlying the cytotoxic effect exerted by the various DP-BFAs, two established markers for apoptosis, caspase-3 activity and DNA fragmentation (Lincz (1998) Immunol. Cell Biol. 76: 1–19), were studied.

Neuro2a neuroblastoma cells (ATCC, CCL-131) were seeded in MEM containing 2 mM L-glutamine, 100 units/ml penicillin, 100 ug/ml streptomycin and 10% FCS at 37° C. 24 hours later, when cells were in logarithmic growth phase, 3,12-DEG-PC was added to a final concentration of 25 μM, 50 μM or 100 μM. Cells grown in the presence of vehicle only served as control group.

Assays for caspase-3 activity and DNA-fragmentation were performed on cell lysates obtained following, respectively, 6 and 24 hours incubation with the drug. Caspase-3 activity was assayed using the fluorogenic substrate Ac-DEVD-AMC (Pharmingen, Becton Dickinson, cat. no. 66081U) and following the manufacture's instructions. DNA-fragmentation was quantified by using the Cell Death Detection Elisa plus kit (Roche, cat. no. 1774 425) and following the manufacture's instructions.

The results are summarized in Table 4. The measured caspase activity is expressed as percentage of the activity in the control plates normalized to protein content. DNA-fragmentation is expressed as OD values at λ=405 nm and is an average of readings from duplicate cell culture lysates.

TABLE 3

Toxicity of DP-BFAs on various cell lines

| Cell line | Caco-2 | C6 glioma | Neuro2a | SKBR | HL60 | U937 | Normal primary fibroblasts | Normal bone marrow | Normal primary epithel |
|---|---|---|---|---|---|---|---|---|---|
| Compound | | | | $EC_{50}$ (μM) | | | | | |
| 3,12-Na | 100 | | 76 | 130 | | 68 | | | |
| 3,12-PO$_4$-Na$_2$ | >200 | | 105 | >200 | | 90 | | | |
| 3,12-MEG-PO$_4$Na$_2$ | >200 | | 60 | >200 | | 75 | | | |
| 3,12-DEG-PO$_4$Na$_2$ | 40 | 38 | 58 | 60 | | 25 | 65 | 62 | >200 |
| 3,12-(ether)-DEG-PO$_4$Na$_2$ | 47 | 40 | 37 | 58 | | 10 | 65 | 68 | >200 |
| 3,12-PC | 150 | | | 62 | 47 | | | | |
| 3,12-MEG-PC | 75 | | 70 | 50 | 20 | 9 | 160 | 95 | 94 |
| 3,12-DEG-PC | 113 | 95 | 134 | 40 | 11 | 6 | 170 | 166 | 90 |
| 3,18-DEG-PC | | | | | 13 | 6 | | 80 | 60 |
| 3,14-PC | | | | | 7 | 4 | | 160 | 72 |

TABLE 4

Apoptosis markers in Neuro2a cells treated with 3,12-DEG-PC

| Added drug | Caspase activity (% of control) | DNA fragmentation (OD$_{405\ nm}$) |
|---|---|---|
| None (Control) | 100% | 0.030 |
| 3,12-DEG-PC, 25 µM | 210% | 0.036 |
| 3,12-DEG-PC, 50 µM | 540% | 0.153 |
| 3,12-DEG-PC, 100 µM | — | 0.389 |

As can be seen from the results in Table 4, incubation of Neuro2a cells with the compound 3,12-DEG-PC, caused about 5-fold increase in caspase-3 activity, and a significant increase in DNA fragmentation. Similar results were obtained when the compound was tested in another malignant cell line, caco-2, derived from colon carcinoma.

Conclusion: Apoptosis may be a possible mechanism for exerting the cytotoxic effect of phosphocholine derivatives of BFAs in certain malignant cells.

III-b) In Vivo Studies

Example 17

In Vivo Model System for Measuring the Effect of DP-BFA on BBB Permeabilization

Permeabilization of the BBB by DP-BFA was investigated in rat model system by monitoring accumulation in the brain of two markers: a) Evans blue dye (EB), which rapidly binds in vivo with albumin (NW 70 kD) and is an indicator for paracellular transport; and b) Fluorescein sodium salt (F—Na), MW 376 D, which is transported via the cellular space, and enables monitoring transcellular transport. Upon BBB disruption the Evans blue-albumin complex irreversibly accumulates in the intercellular space of the brain. The much smaller tracer fluorescein may be transported intracellularly to occupy both inter and intracellular space in the brain.

Blood brain barrier permeabilization in Sprague-Dawley rats was induced by brief exposure to DP-BFA. The animals were anesthetized with Rampun-Imalgen and DP-BFA test compounds were administered via the external carotid artery retrograde to the brain (Smith, Q. R. *Methods of study. In: Physiology and Pharmacology of the Blood-Brain Barrier.* Ed. Bradbury M. W. B. Spinger-Verlag. Berlin-Heidelberg-NY; 1992: 24–52). The pterygo-palathina artery was ligated to avoid escape of infused solutions towards the external head vasculature. DP-BFA solutions were infused over a period of 30 seconds or half an hour, using a Harvard Apparatus Syringe Pump. Blood flow through carotid communis artery was interrupted only at the time of infusion.

All tested DP-BFA molecules were prepared from stock solutions in either water or ethanol by diluting 200–1000 fold into solution of isosmotic mannitol (5%) in Tromethamine buffer (Sigma) or PBS (pH 7.4)

The markers, Evans blue (EB, 25 mg/ml) and fluorescein (F—Na, 12.5 mg/ml), in 1 ml solution, were injected intravenously immediately following administration of the tested DP-BFA, or after a specific time interval if reversibility of action was investigated. Supportive i.v. infusion of F—Na (12.5 mg/ml–100 µl/min) was performed for 8 minutes. Brains were washed with saline solution (60 ml) 10 min after the intracarotid "flash". Brain ipsilateral and contralateral hemispheres and tumors, where applicable, were homogenized separately with 50% trichloroacetic acid (TCA). The markers concentrations in the cortex and in tumors, where, applicable, were determined spectrofluorometrically (Uyama, O. et al., (1988) *J. Cereb. Blood Flow Metab.* 8, 282–284: Abraham et al., (1996) *Neurosci. Lett.* 208, 85–88). The markers content was calculated as µg marker per one-gram brain tissue. Standard error and Student's test for statistical significance were used.

Example 18

Effect of Branched Chain Fatty Acids of Various Chain Lengths on BBB Permeability At the first stage of the study, BFA molecules of different chain lengths were screened for their effect in permeabilizing the blood brain barrier (BBB).

The experiment was carried out on male Sprague-Dawley rats weighing 250–320 g. The procedure described above in Example 17 was followed.

The effect of the tested compounds on the BBB opening was evaluated by two parameters:

a) efficacy—The degree of BBB opening estimated in terms of accumulation of Evans Blue albumin (µg EB/g brain tissue); and b) potency—measured in terms of $EC_{50}$ and minimal effective concentration (MEC) values. $EC_{50}$ is the concentration of a tested compound producing 50% of the maximal effect of Evans Blue extravasation. MEC is defined as the concentration which enables accumulation of three times the amount of Evans blue accumulated in control animals, in our case a total of 3 µg EB/g brain. The lower the $EC_{50}$ and MEC values are, the higher the potency of the tested compound.

The results of evaluation of the effects of different DP-BFAs on BBB permeability are presented in Table 5.

TABLE 5

Effects of branched chain fatty acids on BBB permeability

| Molecule | $EC_{50}$ (µM) | MEC | µg EB/g brain (at $EC_{50}$) |
|---|---|---|---|
| 3,7-Na | >450 | — | 0.8 |
| 3,10-Na | ~700 | — | 08 |
| 3,12-Na | 20 ± 3 | 6.5 ± 0.7 | 32 ± 4 |
| 3,14-Na | 40 ± 5 | 9.1 ± 12 | 16.5 ± 2.5 |
| 3,16-Na | 137 ± 17 | 18 ± 2 | 34 ± 5 |
| 7,7-Na | 184 ± 21 | 132 ± 19 | 4.2 ± 0.6 |

As can be seen from the results in Table 5, there is substantial variation in the degree of Evans Blue extravasation depending on the DP-BFA chain length. Those molecules with the shortest chain length are almost completely ineffective in this model system. The molecules with the highest efficacy were BFAs 3,12-Na and 3,16-Na, each elicits accumulation of more than 30 µg EB/g brain. In the experimental system used, 3,12-Na is the most potent permeabilizing agent, having the lowest $EC_{50}$ and MEC values among the tested compounds.

Conclusion: Under the conditions of the experimental system employed, BFA 3/12-Na was found to be the most effective permeability enhancer in terms of both potency and efficacy. Therefore, DP-BFA derivatives based on BFA-3,12 were studied in more details.

Example 19

Effect of Different DP-BFAs on BBB Permeability

The effect of various DP-BFAs on BBB permeability was tested in the model system of rat brains, as described above in Example 17. Efficacy, namely the level of the BBB opening was expressed as the amount of Evans blue accumulated in the brain (μg EB/g brain). Potency of the tested molecules was estimated by their calculated $EC_{50}$ and minimal effective concentration (MEC) values.

TABLE 6

Effect of different DP-BFAs on BBB permeability (in rat brains)

| Molecule | $EQ_{50}$ (μM) | MEC | μg EB/g brain (at $EC_{50}$) |
|---|---|---|---|
| 3,12-$PO_4$-$Na_2$ | 55 ± 1 | 3.3 ± 0.5 | 20 ± 3 |
| 3,14-$HPO_4$-Na | 67 ± 11 | 6.2 ± 0.9 | 10 ± 1 |
| 7,7-$HPO_{4-Na}$ | 150 | — | 1 |
| 3,12-MEG-$PO_4Na_2$ | 18 ± 3 | 11 ± 2 | 5 ± 1 |
| 3,12-DEG-$PO_4Na_2$ | 20 ± 2 | 3.3 ± 0.5 | 18 ± 3 |
| 3,12-(ether)-DEG-$PO_4Na_2$ | 54 ± 5 | 7.3 ± 1.4 | 26 ± 5.2 |
| 3,12-PC | 76 ± 14 | 23 ± 4 | 10 ± 1 |
| 3,12-MEG-PC | 19.5 ± 1.5 | 10 ± 1 | 15 ± 2 |
| 3,12-DEG-PC | 70 ± 12 | 15 ± 2 | 14 ± 2 |
| Mannitol | 25% | — | 10 ± 2 |

As can be seen in Table 6, various DP-BFAs molecules promote the passage of the albumin bound to the Evans Blue tracer across the BBB. The tested compounds differ in their potency and efficacy.

Under the conditions of this experiment, the most potent derivative of 3,12-BFA was 3,12-DEG-$PO_4Na_2$ having an $ED_{50}$ value of 20 μM and minimal effective concentration (MEC) of 3.3 μM. The most effective compounds in increasing BBB permeability were 3,12-(ether)-DEG-$PO_4Na_2$, 3,12-$PO_4Na_2$ and 3,12-DEG-$PO_4Na_2$. The accumulation levels of Evans Blue dye in rat brain after treatment with $EC_{50}$ concentrations of the 3,12-(ether)-DEG-$PO_4Na_2$, 3,12-$PO_4$—$Na_2$ and 3,12-DEG-$PO_4Na_2$ compounds were, respectively, 26, 20 and 18 μg EB/g brain.

Example 20

Effect of DP-BFA on Transport of Evans Blue Bound Albumin and Fluorescein Across the BBB The effect of various DP-BFAs on BBB permeabilization to molecules of different sizes was examined in vivo in the model system of normal rat brains.

The transport of two markers was followed: a) Evans blue bound to albumin (MW 70 kD) as an indicator for paracellular transport; and b) Fluorescein sodium salt (MW 376 D) that represents small size molecules.

The Evans blue dye (EB) and Fluorescein sodium salt (F—Na) were infused into the artery carotis externa over 30 seconds according to the protocol described above in Example 17. The test compounds were used at their $EC_{50}$ concentrations. Control animals were treated with vehicle solution.

Evans blue extravasation is expressed as the percentage of the total amount of EB accumulated per one gram of brain tissue. The transport of fluorescein into the brain, which is dependent on the serum concentration of this molecule, is presented as percentage of the F—Na level in the serum.

The ratio of accumulation in the brain of F—Na to EB was calculated and the results are presented in Table 7.

TABLE 7

Effect of different DP-BFAs on BBB permeability to EB-albumin and to Fluorescein

| Molecule | % F-Na/ g brain | % EB/ g brain | Ratio * F-Na/EB |
|---|---|---|---|
| control | 0.3 ± 0.08 | 0.04 ± 0.01 | 9.5 ± 1.6 |
| Mannitol- 25% | 2.4 ± 0.4 | 0.6 ± 0.21 | 4.0 ± 0.5 |
| 3,14-Na | 3.8 ± 0.5 | 0.8 ± 0.07 | 4.7 ± 1.7 |
| 3,12-Na | 6.4 ± 1.1 | 1.8 ± 0.2 | 4.9 ± 0.9 |
| 3,12-$PO_4$-$Na_2$ | 8.2 ± 0.9 | 2.9 ± 0.6 | 5.9 ± 1.0 |
| 3,12-MEG-$PO_4$-$Na_2$ | 5.0 ± 0.8 | 0.8 ± 0.1 | 8.4 ± 0.9 |
| 3,12-DEG-$PO_4$-$Na_2$ | 9.0 ± 1.4 | 1.4 ± 0.2 | 9.0 ± 1.2 |
| 3,12-(ether)-DEG-$PO_4Na_2$ | 4.4 ± 0.9 | 4 ± 0.8 | 1.1 ± 0.2 |
| 3,12-PC | 3.0 ± 0.5 | 0.8 ± 0.1 | 7.8 ± 1.3 |
| 3,12-MEG-PC | 5.2 ± 0.8 | 0.9 ± 0.2 | 6.9 ± 0.1 |
| 3,12-DEG-PC | 2.9 ± 0.5 | 0.6 ± 0.1 | 6.8 ± 0.8 |

\* - mean of individual ratios

As can be seen in Table 7, normal BBB (=control) is about 10 times more permeable to Fluorescein than to EB-albumin complex. The hyperosmotic permeabilizer, mannitol, increased BBB permeability to EB to a greater extent than to F—Na (F—Na/EB ratio equals 4). Similarly the tested branched fatty acids 3,14-Na and 3,12-Na showed F—Na/EB ratios of 4.7 and 4.9, respectively.

The different phospho-derivatives of BFA affect BBB permeability to the two markers in a differential fashion. It was found that 3,12-$PO_4$ increased permeability of the BBB to EB-albumin complex about 1.5 times more than the increase in permeability to Fluorescein. On the other hand, it was found that 3,12-DEG-$PO_4$ increased permeability of the BBB in a more physiological manner, i.e. increased F—Na transport to the same extent as EB extravasation. The F—Na/EB ratio in the rat brains exposed to 3,12-DEG-$PO_4$ was around 9.

Conclusions: Various DP-BFA compounds affect BBB permeability in different manners. Some DP-BFAs, e.g. 3,12-(ether)-DEG-$PO_4Na_2$ and 3,12-$PO_4$ (respective F—Na/EB ratios of 1.1 and 5.9) induced selective opening of the BBB which favors transport of large molecules over molecules with low molecular weight. In contrast other molecules, e.g. 3,12-DEG-$PO_4$, equally increased transport of both small molecules such as F—Na and larger molecules such as EB-albumin.

Example 21

Duration of the Effect of DP-BFA on BBB Opening

The effects of DP-BFA on Evans Blue and Fluoroscein extravasation in rat brain were examined at various time points following DP-BFA administration.

Various DP-BFA compounds were infused, over a period of 30 seconds, into the external carotid artery of Sprague Dawley rats, following the procedure described above in Example 17. The tested compounds were used at their $EC_{50}$ concentrations. Evans Blue and Fluoroscein extravasation in the brain was determined 10, 30, 60, 120 and 240 minutes following DP-BFA administration. The content of Evans Blue (μg/g) and Fluoroscein (% of serum) in rat brain was calculated using an average of 2–3 individual animals per time point.

The results obtained in the experimental system as described above demonstrate that the DP-BFA effect on the BBB permeabilization is reversible. Moreover, it is suggested that the BBB opening effects of DP-BFA are relatively short lived. Most tested derivatives of DP-BFA-3,12 maintain BBB permeability for less than one hour, having $D_{1/2}$ of around 30 minutes. $D_{1/2}$ is defined as the duration of at least 50% opening of the BBB using $EC_{50}$ concentrations of the tested compounds. Two compounds, 3,12-PC and 3,12-MEG-PC, both comprising a phosphocholine moiety, have shown $D_{1/2}$ which was 4 times longer than the other tested 3,12-BFA derivatives, i.e. $D_{1/2}$ of around 120 min.

Conclusions: DP-BFA was shown to affect BBB opening in the rat brain in a reversible manner. Various DP-BFA have different durations of the permeabilization effect.

Example 22

Toxicology and Safety Studies

DP-BFA molecules were evaluated for safety and toxicity. Increasing doses of the tested compounds were administered intra-arterially (i.a.) into rats following the protocol described above in Example 17. Animal viability was monitored for 24 hours to evaluate lethal concentrations (LC). LC is defined as the minimal concentration that caused death.

TABLE 8

Comparative safety data of different DP-BFAs (in rats)

| Molecule* | LC (µM) | MEC | Safety LC/MEC |
|---|---|---|---|
| 3,12 | 40 ± 10 | 6.5 ± 0.7 | 6.1 |
| 3,14 | 78 ± 11 | 9.1 ± 1.2 | 8.6 |
| 3,16 | 431 ± 55 | 18 ± 2 | 23.9 |
| 7,7 | 360 ± 67 | 132 ± 19 | 2.7 |
| 3,12-PO$_4$ | 63 ± 12 | 3.3 ± 0.5 | 19.1 |
| 3,14-PO$_4$ | 134 ± 18 | 6.2 ± 0.9 | 21.6 |
| 3,12-MEG-PO$_4$ | 80 ± 15 | 11 ± 2 | 7.5 |
| 3,12-DEG-PO$_4$ | 30 ± 5 | 3.0 ± 0.5 | 10 |
| 3,12-PC | 80 ± 16 | 23 ± 4 | 3.5 |
| 3,12-MEG-PC | 15 ± 2 | 10 ± 1 | 1.5 |
| 3,12-DEG-PC | 300 ± 60 | 15 ± 2 | 20 |

* sodium salt

Safety index is defined as the ratio between the lethal dose (LC) and the minimal effective concentration (MEC), wherein MEC corresponds to a calculated concentration of the tested compound that elicits accumulation of three times the amount of Evans blue accumulated in control animals treated with vehicle only, i.e. total accumulation of 3 µg EB. The higher the LC/MEC ratio is, the higher the safety index.

Conclusions: Introduction of a phosphate group increased safety index by 2–3 folds without significantly hampering potency.

Example 23

In Vivo Model System for Measuring the Effect of DP-BFA on BTB Permeabilization (Tumor-bearing Rats)

In order to study the ability of DP-BFA compounds to modulate blood tumor barrier (BTB), a model system of C6 glioma-bearing rats, was employed.

Sprague Dawley (SD) rats were inoculated with C6 gliosarcoma cells following the procedure described by Bartus et al. (*Exp Neurol* (1996); 142:14–28). A small burr-hole was made in the frontal scalp bone of the rat fixed in a stereotaxis apparatus. Using a Hamilton syringe, 10 µl or 5 µl of media, containing 2.5×10$^5$ C6 gliosarcoma cells were inoculated into the frontal cortex. Coordinates were 1 mm posterior of bregma, 2.5 mm—lateral, and 3 mm—depth. The needle remained in the place for 5 min. After removal of the needle, fascia and scalp were sutured. The rats were checked 6–8 days after inoculation, when tumors of sufficient size (20–60 mg) had developed. The tumor was weighed after F—Na visualization and dissection. Parts of the rats' brains were subject to histological examinations and monitored for Evans Blue and Fluorescein uptake into ipsilateral tumour tissue, peritumoural tissue and contralateral tissue.

Results (not shown) obtained from experiments conducted on control tumor-bearing rats (not treated with the compounds of the invention) demonstrated that permeability of the blood tumor barrier (BTB) for EB and fluorescein is, respectively, about 2-fold and 4-fold higher than that found for the intact BBB.

Example 24

Effects of Various BFAs Molecules on BBB and BTB Opening (Study in Tumor-bearing Rats)

The bilateral tumor model system of C6 glioma-bearing rats described in Example 23 above was employed for screening of various derivatives of DP-BFA for their ability to permeabilize the blood brain barrier (BBB) in comparison to their effect on the blood tumor barrier (BTB). The experimental procedure described in Example 23 was followed except that the tumor-bearing rats were further treated with DP-BFA. The tested compounds, at concentrations around their $EC_{50}$ values, were unilaterally infused into the external carotis artery over 30 seconds as described in Example 17. Animals treated with vehicle only serve as a control group. Permeabilization effect was quantitated by measuring accumulation of albumin bound Evans blue dye in tumor (T) versus non-tumor (NT) tissues.

Calculated efficacy values and specificity indices are summarized in Table 9. Specificity index is defined as the ratio between the levels of EB accumulated in tumor and those accumulated in non-tumor brain tissues (T/NT).

TABLE 9

Comparison of the BBB and BTB opening by various DP-BFAs

| Molecule | $EC_{50}$* (µM) | BTB EB µg/g Tumor | BBB EB µg/g Non-tumor brain | Specificity Tumor/ Non-tumor |
|---|---|---|---|---|
| 3,12-Na | 22 ± 4 | 44 ± 8 | 43 ± 9 | 1.1 ± 0.3 |
| 3,12-PO$_4$ | 10 ± 2 | 14 ± 6 | 2.5 ± 1.5 | 6.3 ± 1.3 |
| 3,12-MEG-PO$_4$ | 22 ± 3 | 25 ± 3 | 21 ± 4 | 1.2 ± 0.2 |
| 3,12-DEG-PO$_4$ | 7 ± 2 | 34 ± 8 | 2.0 ± 0.2 | 22 ± 5 |
| 3,12-PC | 52 ± 7 | 17 ± 2 | 10 ± 2 | 1.8 ± 0.5 |
| 3,12-MEG-PC | 20 | 12 | 6 | 2 |
| 3,12-DEG-PC | 60 | 11 | 5 | 2 |
| Mannitol | 25% | 12 ± 2 | 7 ± 2 | 2.1 ± 0.5 |

* $EC_{50}$ values for tumor-bearing rats

As can be seen in Table 9, most tested compounds have shown similar levels of EB accumulation in tumor and in non-tumor brain tissues, i.e. T/NT ratios of about 1 to 2. With mannitol (25%) the EB accumulation in the tumor was about twice the accumulation in the non-tumor brain. In the experimental system used, the compound, 3,12-DEG-PO$_4$, showed high specificity for opening the tumor blood barrier (BTB) manifested as EB accumulation in tumor which was 22 times higher than the EB levels in the non-tumor tissue (T/NT ratio=22).

Conclusion: 3,12-DEG-PO$_4$ showed the most specific effect on opening the BTB in C6 glioma tumors. This compound permeabilizes the blood tumor barrier (BTB) of C6 gliomas to a greater extend than the normal blood brain barrier (BBB). DP-BFA derivatives may, thus, serve as agents capable of specific and selective opening of the BTB.

Example 25

Unilateral DP-BFA Administration in SD Tumor-bearing Rats

Figure 2A:
FIGS. 2A–C depict Evans blue accumulation in brain sections of rats bearing bilateral gliomas following unilateral administration of a compound as follows: 10 μM 3,12-DEG-HPO$_4$Na (FIG. 2A), 40 μM 3,12-Na (FIG. 2B) or mannitol 25% (FIG. 2C).
Figure 2B:
Figure 2C:
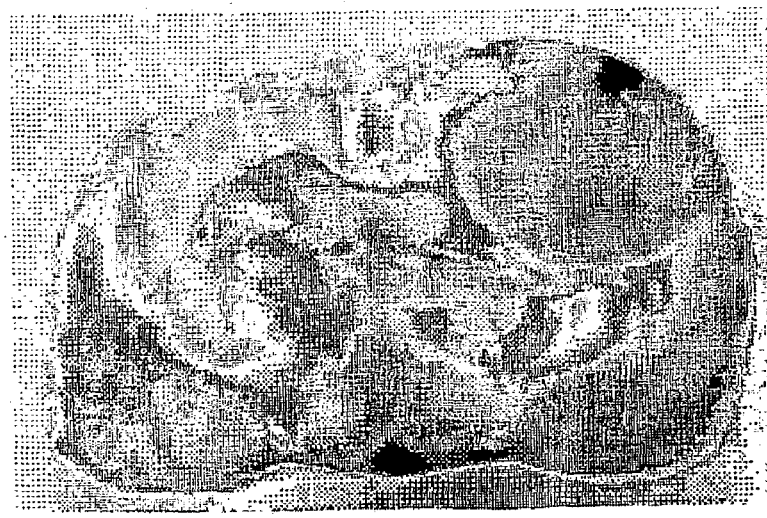

Evans Blue and Fluoroscein penetration into gliomas tumors was examined following unilateral infusion into the external carotis artery of either 10 μM 3,12-DEG-HPO$_4$Na (FIG. 2A), 40 μM 3,12-Na BFA (FIG. 2B) or 25% mannitol (FIG. 2C). The relevant compound was infused into rat brains at 9 to 12 days following inoculation of C6 glioma cells as described in Example 23.

It may be clearly seen from FIG. 2A Nat the Evans Blue staining following 3,12-DEG-PO$_4$ administration to rats with bilateral gliomas is only in the tumor tissue in the ipsilateral hemisphere. On the other hand, the carbo counterpart of the DP-BFA, i.e. BFA 3,12, and the hyperosmotic agent, mannitol, equally permeabilized tumor and non-tumor brain tissues.

Example 26

Effect of DP-BFA on Blood Retinal Barrier (BRB) Permeabilization

Permeabilization of the blood retinal barrier (BRB) by DP-BFA was investigated in rats by monitoring leakage of the fluorescent marker, fluorescein sodium salt (F—Na), from the blood vessels in the sclera.

Sprague-Dawley (SD) rats, weighing from 250 to 350 grams, were anesthetized with a solution of Ketamin (100 mg/ml) and Xylasine (2%) injected at 0.1 ml/100 g body weight. The anesthetized animals were injected with 0.25 ml F—Na (12.5 mg/ml) into the jugular vein. The retinal blood vessels were recorded with a 3-CCD color camera (teli CS5850) attached with a c-mount to the INAMI L-0960 microscope for ophthalmic surgery. The microscope is equipped with a light source and an appropriate filter for F—Na detection. After 10 min the retina was cleared from the F—Na. At this point, 1.5 ml of 3,12-DEG-HPO$_4$Na (12.5 μg/ml) was intra-arterially injected over a period of 30 seconds, accompanied with a second i.v. injection of F—Na. Pictures of the blood vessels were taken at t=0 and 0.25, 0.5, 1, 2, 4, 8 and 10 minutes following administration of the drug. The same experiment was repeated in a second group of control rats, where 1.5 ml of vehicle (Tab-mannitol 5%) was intra arterially injected instead of 3,12-DEG-HPO$_4$Na.

By monitoring the distribution of F—Na in the blood vessels at the posterior part of the animal eye, at the retina level, it was demonstrated that by 10 minutes following administration of F—Na alone, all the fluorescent dye was completely cleared from the area surrounding the retinal blood vessels. However, i.v. injection of F—Na in combination with i.a. injection of 3,12-DEG-HPO$_4$Na, results in F—Na accumulation around the blood vessels at the retinal level. This leakage of F—Na from the blood vessels, in the presence of 3,12-DEG-HPO$_4$Na, is an indication for the permeabilization of the blood retinal barrier. In the control animals, where only vehicle was administered instead of the DP-BFA drug, the results were similar to those in the animals injected with F—Na alone, namely by 10 minutes following administration, no fluorescence could be detected in the blood vessels or at the area surrounding them at the retinal level. The results depicted in FIGS. 3A–C represent angiographia of the eye, namely pictures of the eye blood supply imaging taken at the retinal level as recorded at 30 seconds and 10 minutes following administration of F—Na either alone (FIG. 3A), or in combination with 3,12-DEG-HPO$_4$Na (FIG. 3B) or vehicle (FIG. 3C).

Figure 4A:
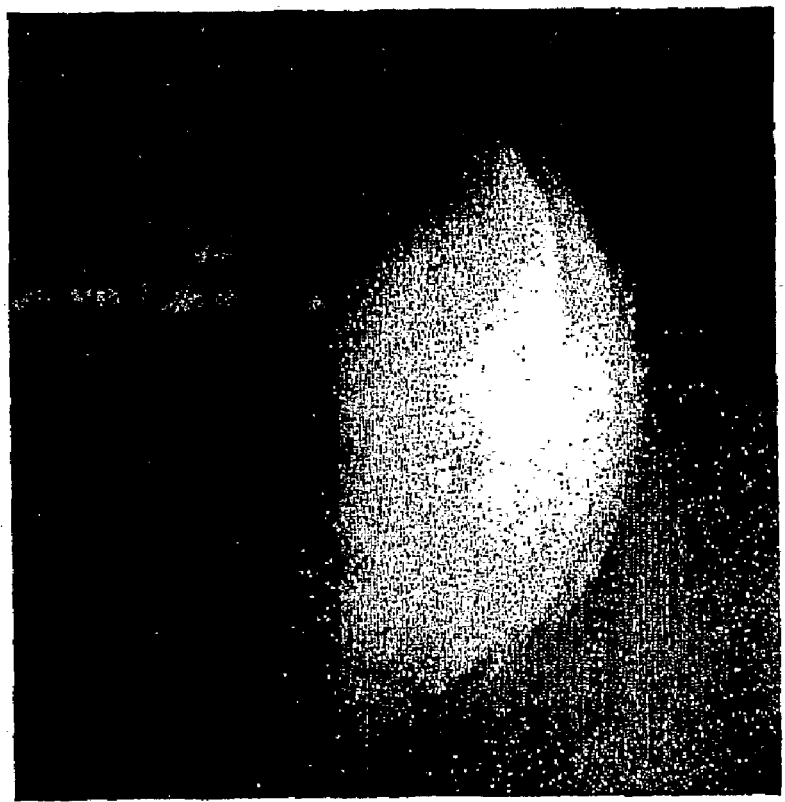
FIGS. 4A–B depict F—Na accumulation at the anterior part of the eye as recorded 10 minutes after F—Na administration accompanied with either 3,12-DEG-HPO$_4$Na (FIG. 4A) or vehicle (FIG. 4B) following the procedure described in Example 26.
Figure 4B:

In accordance with this observation, at 10 minutes following the F—Na administration, higher amounts of F—Na could be detected in the vitreous of the animals treated with 3,12-DEG-HPO$_4$Na, than in the vitreous of the control animals that were injected with the F—Na and vehicle only (FIGS. 4A–B). The accumulation of the fluorescent signal at the vitreous is due to the BRB permeabilization and F—Na leakage from the blood vessels at the retinal level.

Conclusion: 3,12-DEG-HPO$_4$Na enables permeabilization of the blood retina barrier, and results in F—Na accumulation in the retina and vitreous.

Example 27

Anti-tumor Activity of DP-BFA

The anti-tumor effects of various P-BFAs were studied in the in vivo model system described above in Example 17. Tested P-BFAs were intra-arterially administered at the concentrations previously determined as being effective in permeabilization of the BBB and BTB for Evans blue and Fluorescein extravasation. The experimental procedure for tumor inoculation, as described in Example 23, was followed.

On Day 3–4 following inoculation of the C6 gliosarcoma cells, rat were cannulated through external carotid artery and the tested P-BFAs were infused over 30 seconds, as described in Example 17, except that in this experiment no markers were administered. The treated rats were maintained until Day 7–9, and then sacrificed. Coronal sections were obtained, stained by eosin-hematoxylin, and reviewed histologically to determine tumor volume. Animals treated with vehicle only serve as control. Standard error and Student's test for statistical significance were used. The results are summarized in Table 10.

As can be seen from the results in Table 10, P-BFA compounds exhibit cytostatic effect on glioma tumor growth in vivo. Under the experimental conditions employed, the 3,12-DEG-PO$_4$ compound exhibited the most pronounced anti-tumor effect. Other compounds, e.g. 3,12-MEG-PC, also demonstrated a significant anti-tumor activity, though to a lesser degree.

Conclusion: P-BFAs intra-arterially administered into C6 glioma-bearing rats exhibit cytotoxic effect on the tumor.

TABLE 10

Anti-tumor effects of various P-BFAs on tumor growth

| Molecule | P-BFA Concentrations (μM) | Tumor volume (mm³) ± SE | P (to control) |
|---|---|---|---|
| Control | 0 | 8.1 ± 2.22 | — |
| 3,12-MEG-HPO₄Na | 30 | 4.2 ± 1.6 | >0.1 |
| 3,12-PC | 50 | 3.8 ± 0.8 | >0.1 |
| 3,12-MEG-PC | 10 | 2.88 ± 0.6 | <0.05* |
| 3,12-DEG-PC | 60 | 3.9 ± 1.0 | >0.1 |
| 3,12-DEG-HPO₄Na | 5 | 1.5 ± 0.3 | <0.01* |
| 3,12-DEG-PO₄Na₂ | 30 | 1.6 ± 0.4 | <0.01* |

SE - standard error of the mean,
* - statistically significant difference.

Example 28

Anti-tumor Effect of DP-BFA

The anti-tumor effect of DP-BFA was evaluated by monitoring tumor volume and appearance in a model system of C6 glioma-bearing rats. Sprague Dawley (SD) rats were inoculated with 2.5×10⁵ C6 glioma cells in 5 μl PBS as follows. Rats were mounted into a stereotactic head holder in a flat-skull position. After reflections of the periosteum, a burr hole was preformed with a 1 mm drill in the following coordinates: bregma—1.0, 3.50 mm lateral from the midline on the left side, and at a depth of 3.50 mm. The cell suspension was manually injected at a depth of 3.50 mm using a 10 μl Hamilton syringe. The tumor bearing rats were treated 72 h post inoculation with a single dose, ranging from 5 to 20 μM, of 3,12-di-ethylenglycol phosphate (3,12-DEG-PO₄; sodium salt) or vehicle (iso-osmotic buffer, pH=7.4) infused into the external carotid artery for 30 sec. at a velocity of 3 ml/min.

The pterigo-palatina artery was legated, and the common carotid artery was clamped at the time of infusion.

Five days after the inoculation of the C6 tumor cells, the rats were anesthetized with Ketamin/xylazin (1:1) 0.1 ml/100 grams body weight, perfused with saline and fixed with 4% Formaldehyde solution. Brains were removed and cryoprotected in a sucrose solution for 48 h. The brains were then sliced in coronal section, stained with Haematoxylin-Eosine and underwent pathology evaluation.

A significant decrease in the tumor size was observed in the treated animals in comparison to the non-treated animals. Tumor volume was 8.1±2.2 mm³ (N=7) in the vehicle-treated animals and 1.6±0.2 mm³ (N=12) in the animals treated with 3,12-DEG-PO₄. In addition, the microenvironment and the nature of the tumor growth were different. Vehicle treated tumor-bearing rats exhibited a remarkable local cell expansion in the cortex, white matter and meninges. The C6 gliomas appeared irregular and highly infiltrative and showed a high tendency to invade through the perivascular lymphatic spaces. In contrast, the treatment with DP-BFA, given once on the 3rd day after cells inoculation, significantly changed the character of the tumor growth. The C6 glioma invasiveness through the perivascular spaces was diminished and a solid tumor with defined border was observed. Some limited invasion was found into the meninges around the inoculation area and sub-ependima.

Conclusion: 3,12-DEG-PO₄ showed a significant anti-tumor effect as inhibiting tumor invasiveness and rate of growth. Thus, DP-BFA compounds may be useful in inhibiting spreading and invasiveness of tumors.

The skilled artisan will appreciate that the principles of the present disclosure are amenable to many embodiments and variations or modifications, all of which are within the scope of the invention. The examples are intended to be construed as non-limitative, and the scope of the invention is to be defined by the claims which follow.

The invention claimed is:

1. A compound of the formula I:

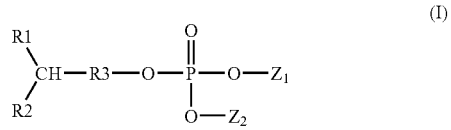

or a pharmaceutically acceptable salt thereof, wherein:
R1 and R2 are the same or different, saturated or unsaturated aliphatic chain having from 2 to 30 carbon atoms;
R3 is $A\text{-}[CH_2]_m\text{-}B[CH_2]_n\text{—}C\text{—}[CH_2]_p\text{-}D$, wherein m, n and p are each independently zero or an integer from 1 to 12, and A is carbonyl or oxygen, B is oxygen or a covalent bond, C is oxygen or a covalent bond, D is a covalent bond with the proviso that no two oxygen atoms are directly connected to each other; and
one of $Z_1$ and $Z_2$ is absent and the other together with the phospho group forms a phospho ester of glycerol, choline, ethanolamine, inositol, or serine.

2. The compound according to claim 1, wherein R1 is 3 carbon atoms in length and R2 is from 12 to 18 carbon atoms in length.

3. The compound according to claim 1, wherein R1 is propyl and R2 is dodecyl.

4. The compound according to claim 1, wherein R3 is mono-ethylene glycol or di-ethylene glycol moiety.

5. The compound according to claim 1, wherein the total number of carbon atoms in R2 and R3 together is from 6 to 26.

6. The compound according to claim 1, wherein the total number of carbon atoms in R2 and R3 together is from 16 to 22.

7. The compound according to claim 1, wherein $Z_1$ together with the phospho group form a phospho ester of choline.

8. The compound according to claim 1 selected from the group consisting of:
2-(4-Hexadecanoyloxy)ethyl phosphocholine (3,12-MEG-PC),
2-(4-Hexadecanoyloxy)ethoxyethyl phosphocholine (3,12-DEG-PC),
2-{2'-[10''-(Hexadecyl-4-oxy)decyl-1-oxy]ethoxy}ethylphosphocholine (3,12-O—C₁₀-DEG-PC),
2-(4-Octadecanoyloxy)ethyl phosphocholine (3,14-MEG-PC),
2-(4-Octadecanoyloxy)ethoxyethyl phosphocholine (3,14-DEG-PC),
2-(4-Eicosanoyloxy)ethyl phosphocholine (3,16-MEG-PC),
2-(4-Eicosanoyloxy)ethoxyethyl phosphocholine (3,16-DEG-PC), and 2-(2'-Propyleicosanoyloxy)ethoxy ethylphosphocholine (3,18-DEG-PC).

9. The compound according to claim 1 which is 2-(4-Hexadecanoyloxy)ethyl phosphocholine.

10. The compound according to claim 1 which is 2-(4-Hexadecanoyloxy)ethoxyethyl phosphocholine.

11. A pharmaceutical composition comprising a pharmaceutically acceptable carrier and a compound of the formula I, or a pharmaceutically acceptable salt thereof,

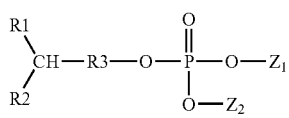

(I)

wherein:
R1 and R2 are the same or different, saturated or unsaturated aliphatic chain having from 2 to 30 carbon atoms;
R3 is A-$[CH_2]_m$—B—$[CH_2]_n$—C—$[CH_2]_p$-D, wherein m, n and p are each independently zero or an integer from 1 to 12, and A is carbonyl or oxygen, B is oxygen or a covalent bond, C is oxygen or a covalent bond, D is a covalent bond with the proviso that no two oxygen atoms are directly connected to each other; and
one of $Z_1$ and $Z_2$ is absent and the other together with the phospho group forms a phospho ester of glycerol, choline, ethanolamine, inositol, or seine.

12. The pharmaceutical composition according to claim 11, wherein R1 is 3 carbon atoms in length and R2 is from 12 to 18 carbon atoms in length.

13. The pharmaceutical composition according to claim 11, wherein R3 is mono-ethylene glycol or di-ethylene glycol moiety.

14. The pharmaceutical composition according to claim 11, wherein $Z_1$ together with the phospho group form a phospho ester choline.

15. The pharmaceutical composition according to claim 11, wherein the compound of the formula I is selected from the group consisting of:
2-(4-Hexadecanoyloxy)ethyl phosphocholine (3,12-MEG-PC),
2-(4-Hexadecanoyloxy)ethoxyethyl phosphocholine (3,12-DEG-PC),
2-{2'-[10"-(Hexadecyl-4-oxy)decyl-1-oxy]ethoxy}ethylphosphocholine (3,12-O—$C_{10}$-DEG-PC),
2-(4-Octadecanoyloxy)ethyl phosphocholine (3,14-MEG-PC),
2-(4-Octadecanoyloxy)ethoxyethyl phosphocholine (3,14-DEG-PC),
2-(4-Eicosanoyloxy)ethyl phosphocholine (3,16-MEG-PC),
2-(4-Eicosanoyloxy)ethoxyethyl phosphocholine (3,16-DEG-PC), and
2-(2'-Propyleicosanoyloxy)ethoxy ethylphosphocholine (3,18-DEG-PC).

16. The pharmaceutical composition according to claim 11, wherein the compound of the formula I is 2-(4-Hexadecanoyloxy)ethoxyethyl phosphocholine.

17. The compound according to claim 1 which is 2-{2'-[10"-(Hexadecyl-4-oxy)decyl-1-oxy]ethoxy}ethylphosphocholine.

18. The pharmaceutical composition according to claim 11, wherein the compound of the formula I is 2-{2'-[10"-(Hexadecyl-4-oxy)decyl-1-oxy]ethoxy}ethylphosphocholine.

* * * * *